US012582462B2

(12) United States Patent 
Ikuma et al.

(10) Patent No.: US 12,582,462 B2 
(45) Date of Patent: Mar. 24, 2026

(54) ELECTRODE UNIT AND ENDOSCOPE SYSTEM

(71) Applicant: OLYMPUS CORPORATION, Tokyo (JP)

(72) Inventors: Soichi Ikuma, Akishima (JP); Yuji Sakai, Kodaira (JP); Tsuyoshi Hayashida, Hachioji (JP); Takayuki Tsukagoshi, Hino (JP); Kei Kubo, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 1043 days.

(21) Appl. No.: 17/345,678

(22) Filed: Jun. 11, 2021

(65) Prior Publication Data

US 2021/0369327 A1 Dec. 2, 2021

Related U.S. Application Data

(63) Continuation of application No. PCT/JP2018/046175, filed on Dec. 14, 2018.

(51) Int. Cl.
| | |
|---|---|
| *A61B 18/14* | (2006.01) |
| *A61B 17/00* | (2006.01) |
| *A61B 18/00* | (2006.01) |

(52) U.S. Cl.
CPC ........ *A61B 18/149* (2013.01); *A61B 18/1482* (2013.01); *A61B 2017/00991* (2013.01); 
(Continued)

(58) Field of Classification Search
CPC ................................................... A61B 18/149
See application file for complete search history.

(56) References Cited

U.S. PATENT DOCUMENTS

| | | | |
|---|---|---|---|
| 3,939,839 | A | 2/1976 | Curtiss |
| 5,196,011 | A | 3/1993 | Korth et al. |

(Continued)

FOREIGN PATENT DOCUMENTS

| | | |
|---|---|---|
| JP | H05-220172 A | 8/1993 |
| JP | 2000-201945 A | 7/2000 |

(Continued)

OTHER PUBLICATIONS

International Search Report dated Mar. 19, 2019 received in PCT/JP2018/046175.

*Primary Examiner* — Ronald Hupczey, Jr.

(74) *Attorney, Agent, or Firm* — Scully, Scott, Murphy & Presser, P.C.

(57) ABSTRACT

An electrode unit configured to resect or coagulate tissue inside a subject by using a high-frequency current, including: an electrode supporting portion provided with a pair of distal end rigid portions surfaces of which are covered by an electrically insulating material, and an elastic region portion having lower bending rigidity than bending rigidity of each of the pair of distal end rigid portions, the elastic region portion being provided on a proximal end side of each of the pair of distal end rigid portions; and an electrode configured with electrode bodies respectively protruding downward from the pair of distal end rigid portions and an installation portion that installs respective lower ends of the electrode bodies.

15 Claims, 18 Drawing Sheets

(52) U.S. Cl.
CPC .............. *A61B 2018/00589* (2013.01); *A61B 2018/00601* (2013.01); *A61B 2018/1405* (2013.01); *A61B 2018/1475* (2013.01)

(56) References Cited

U.S. PATENT DOCUMENTS

| | | | | |
|---|---|---|---|---|
| 5,810,764 A * | 9/1998 | Eggers ............... | A61B 18/1206 604/23 |
| 5,908,419 A * | 6/1999 | Hahnen ................ | A61B 18/149 606/49 |
| 5,919,191 A * | 7/1999 | Lennox ................ | A61B 18/149 606/50 |
| 6,395,001 B1 | 5/2002 | Ellman et al. | |
| 2001/0053908 A1 * | 12/2001 | Brommersma ...... | A61B 18/149 606/45 |
| 2004/0254571 A1 * | 12/2004 | Iki ...................... | A61B 18/1402 606/41 |
| 2005/0070893 A1 * | 3/2005 | Aue .................... | A61B 18/149 606/46 |
| 2017/0231686 A1 * | 8/2017 | Sartor ................. | A61B 18/149 606/46 |

FOREIGN PATENT DOCUMENTS

| | | |
|---|---|---|
| JP | 2002-095677 A | 4/2002 |
| JP | 3730796 B2 | 1/2006 |

* cited by examiner

ELECTRODE UNIT AND ENDOSCOPE SYSTEM

CROSS REFERENCE TO RELATED APPLICATION

This application is a continuation application of PCT/JP2018/046175 filed on Dec. 14, 2018, the entire contents of which are incorporated herein by this reference.

BACKGROUND OF THE INVENTION

1. Field of the Invention

The present invention relates to an electrode unit and an endoscope system configured to resect or coagulate tissue inside a subject by using a high-frequency current.

2. Description of the Related Art

Electrocautery has been known as a technique of resecting or coagulating tissue of a subject such as a human body. For example, Japanese Patent No. 3730796 discloses a device configured to resect or coagulate tissue inside a subject by using a high-frequency current under observation with an endoscope. The technique disclosed in Japanese Patent No. 3730796 carries out resection or coagulation of tissue by passing a high-frequency current through an electrode formed in a loop shape.

The electrode formed in a loop shape as disclosed in Japanese Patent No. 3730796 is used for, for example, resecting tissue in an organ such as the bladder. For example in the case of using resected tissue for pathological examination, the tissue of a predetermined thickness is required. It is therefore preferable that a thickness of the resected tissue should be constant regardless of the user.

SUMMARY OF THE INVENTION

An electrode unit according to one aspect of the present invention is configured to resect or coagulate tissue inside a subject by using a high-frequency current, and includes: an electrode supporting member provided with a pair of distal end rigid members surfaces of which are covered by an electrically insulating material, and an elastic region member having lower bending rigidity than bending rigidity of each of the pair of distal end rigid members, the elastic region member being provided on a proximal end side of each of the pair of distal end rigid members; and an electrode configured with electrode bodies respectively protruding downward from the pair of distal end rigid members and an installation portion that installs respective lower ends of the electrode bodies.

An endoscope system according to one aspect of the present invention includes the electrode unit.

DETAILED DESCRIPTION OF THE PREFERRED EMBODIMENTS

Hereinafter, preferred embodiments of the present invention are described with reference to the drawings. Note that, in each of the figures used for the following description, components may have different scales so that each of the components has a recognizable size on the figures, and the present invention is not limited to the number, shapes, ratios of size, and relative positional relationships of the components featured in the figures.

First Embodiment

Figure 1:
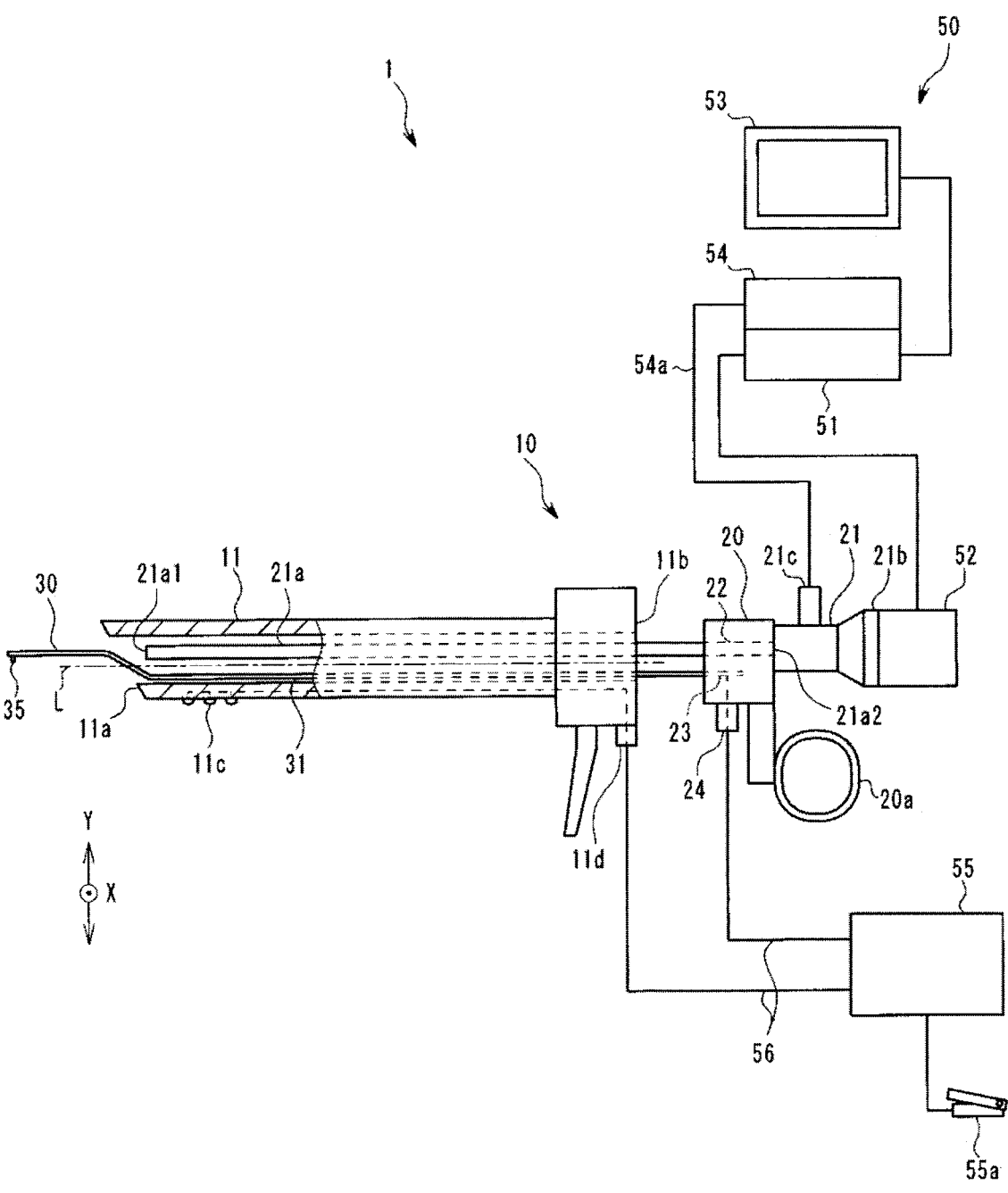
FIG. 1 is a diagram showing a schematic configuration of an endoscope system of a first embodiment.

FIG. 1 is a diagram showing a schematic configuration of an endoscope system 1 of a first embodiment. The endoscope system 1 is a device configured to resect or coagulate tissue inside a subject under observation with an endoscope.

The endoscope system 1 of the present embodiment includes a resectoscope 10, which is an endoscope, an electrode unit 30, and an external device 50. In the present embodiment, the subject is a human body as an example. Although the endoscope in the present embodiment is, as an example, an endoscope typically referred to as a resectoscope, the endoscope may also be a flexible endoscope.

The resectoscope 10 includes a sheath 11, a slider 20, and a telescope 21.

The sheath 11 includes a tubular area along a linear longitudinal axis L. The sheath 11 is an area inserted from the outside of the subject to the inside of the subject during use of the resectoscope 10. The sheath 11 has openings on both ends in a direction along the longitudinal axis L. During use of the resectoscope 10, the telescope 21 and the electrode unit 30 described later are inserted into the sheath 11.

An outer sheath for introducing a perfusate into the subject is arranged on an outer periphery of the sheath 11. A configuration for introducing the perfusate into the subject, such as the outer sheath, is well-known and description of such a configuration is omitted. In the present embodiment, the perfusate is, for example, an electrolyte solution such as physiological saline and is electrically conductive.

Of both ends of the sheath 11 in the direction along the longitudinal axis L, an end on a side to be inserted into the subject is referred to as a "distal end 11a", and an end on an opposite side to the distal end 11a is referred to as a "proximal end 11b". The proximal end 11b of the sheath 11 is exposed to the outside of the subject during use of the resectoscope 10.

For the sake of description hereinafter, a first axis X and a second axis Y are defined, which are a pair of axes orthogonal to the longitudinal axis L and orthogonal to each other. In a direction along the first axis X, one side is defined as a right side and the other side is defined as a left side. In a direction along the second axis Y, one side is defined as an upper side and the other side is defined as a lower side. In the present embodiment, in an image picked up by using the telescope 21, a horizontal direction is substantially parallel to the first axis X, and a perpendicular direction is substantially parallel to the second axis Y, as an example. The upper side and the right side are an upper side and a right side in the image picked up by using the telescope 21.

A collection electrode 11c configured with an electrically conductive material is exposed at least to the surface in the vicinity of the distal end 11a of the sheath 11. Note that it may also be configured that the entire sheath 11 is configured with an electrically conductive material such as a metal and the entire surface of the sheath 11 functions as the collection electrode 11c.

A sheath connector 11d is provided in the vicinity of the proximal end 11b of the sheath 11. The sheath connector 11d is electrically connected to the collection electrode 11c. A cable 56 is connected to the sheath connector 11d. The cable 56 electrically connects between the sheath connector 11d and a high-frequency power control device 55 of the external device 50.

The slider 20 is arranged on a side of the proximal end 11b of the sheath 11. The slider 20 moves relative to the sheath 11 in the direction along the longitudinal axis L. The slider 20 is provided with a handle 20a. When a user applies a force to the handle 20a with fingers, the slider 20 moves relative to the sheath 11 in the direction along the longitudinal axis L. Note that a mechanism for guiding the slider 20 in a relatively movable manner to the sheath 11 is similar to the mechanism of the conventional resectoscope 10, and therefore illustration and description of the mechanism are omitted.

The slider 20 includes a scope holding portion 22, an electrode unit holding portion 23, and an electrode connector 24. The scope holding portion 22 holds the telescope 21.

The telescope 21 is an area for optically observing the inside of the subject. The telescope 21 is provided with an elongated insertion portion 21a, an eye piece 21b, and a light source connection portion 21c. The insertion portion 21a is inserted into the sheath 11 in a state in which the telescope 21 is fixed onto the scope holding portion 22.

An observation window and an illumination light emission window are provided on a distal end portion 21a1 of the insertion portion 21a. The eye piece 21b and the light source connection portion 21c are provided on a proximal end portion 21a2 of the insertion portion 21a.

An image pickup unit 52 is attached to the eye piece 21b. The image pickup unit 52 is electrically connected to a video processor 51 of the external device 50. An image display device 53 is electrically connected to the video processor 51. One end of an optical fiber cable 54a is connected to the light source connection portion 21c. The other end of the optical fiber cable 54a is connected to a light source device 54 of the external device 50.

An image in a field of view from the observation window provided on the distal end portion 21a1 of the insertion portion 21a is picked up by the image pickup unit 52 and displayed on the image display device 53. Illumination light emitted from the light source device 54 is emitted from the illumination light emission window provided on the distal end portion 21a1 of the insertion portion 21a.

Configurations of the telescope 21 and the external device 50 connected to the telescope 21 are similar to the configurations in the conventional resectoscope 10, and therefore detailed description of the configurations is omitted.

The electrode unit holding portion 23 holds the electrode unit 30 described later. The electrode connector 24 is electrically connected to the electrode unit 30 held by the electrode unit holding portion 23. A cable 56 is connected to the electrode connector 24. The cable 56 electrically connects the electrode connector 24 and the high-frequency power control device 55 of the external device 50. Note that the electrode connector 24 may also be formed integrally with the sheath connector 11*d*.

The electrode unit 30 includes an area inserted into the sheath 11 in a state of being fixed onto the electrode unit holding portion 23. The slider 20 moves together with the telescope 21 and the electrode unit 30, relative to the sheath 11 in the direction along the longitudinal axis L. A part of the electrode unit 30 may protrude from the distal end 11*a* of the sheath 11. As described later, an electrode 35 is provided in the area of the electrode unit 30 protruding from the distal end 11*a* of the sheath 11.

The electrode unit 30, the collection electrode 11*c*, and the high-frequency power control device 55 configure a so-called bipolar electro-surgical apparatus. The high-frequency power control device 55 is provided with a switch 55*a*. The switch 55*a* is, for example, a foot switch operated by a user's foot. The high-frequency power control device 55 is configured to switch between presence and absence of output of a high-frequency current according to an operation on the switch 55*a*.

The high-frequency current outputted from the high-frequency power control device 55 flows among the electrode 35, the perfusate, and the collection electrode 11*c* inside the subject. In a state in which the high-frequency power control device 55 outputs the high-frequency current, tissue in the subject in contact with the electrode 35 generates heat, whereby the tissue is resected or coagulated.

Figure 2:
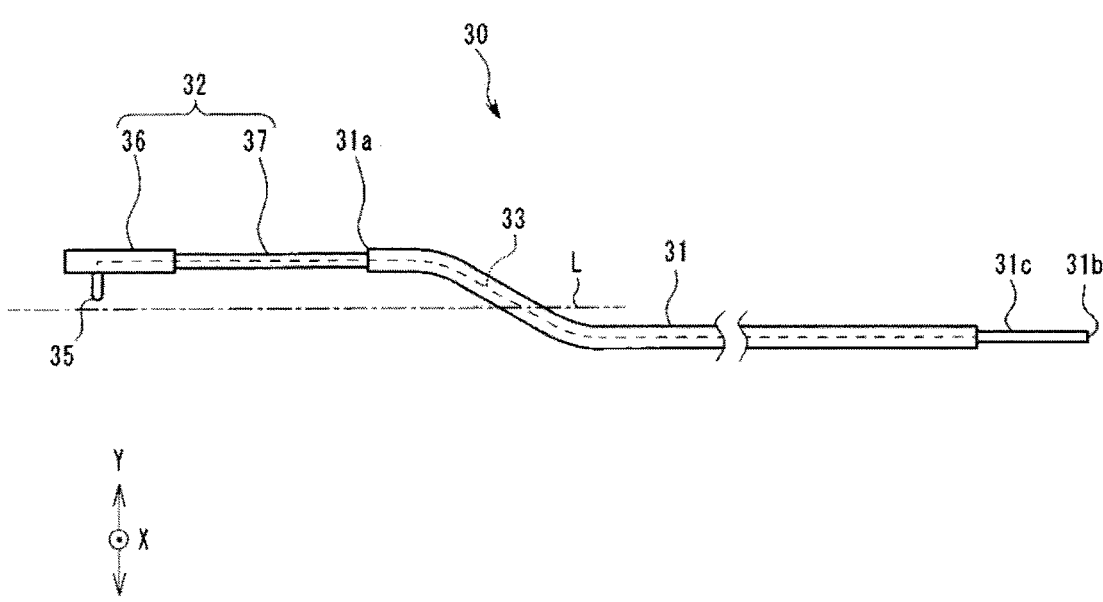
FIG. 2 is a diagram showing an electrode unit of the first embodiment seen along a first axis.
Figure 3:
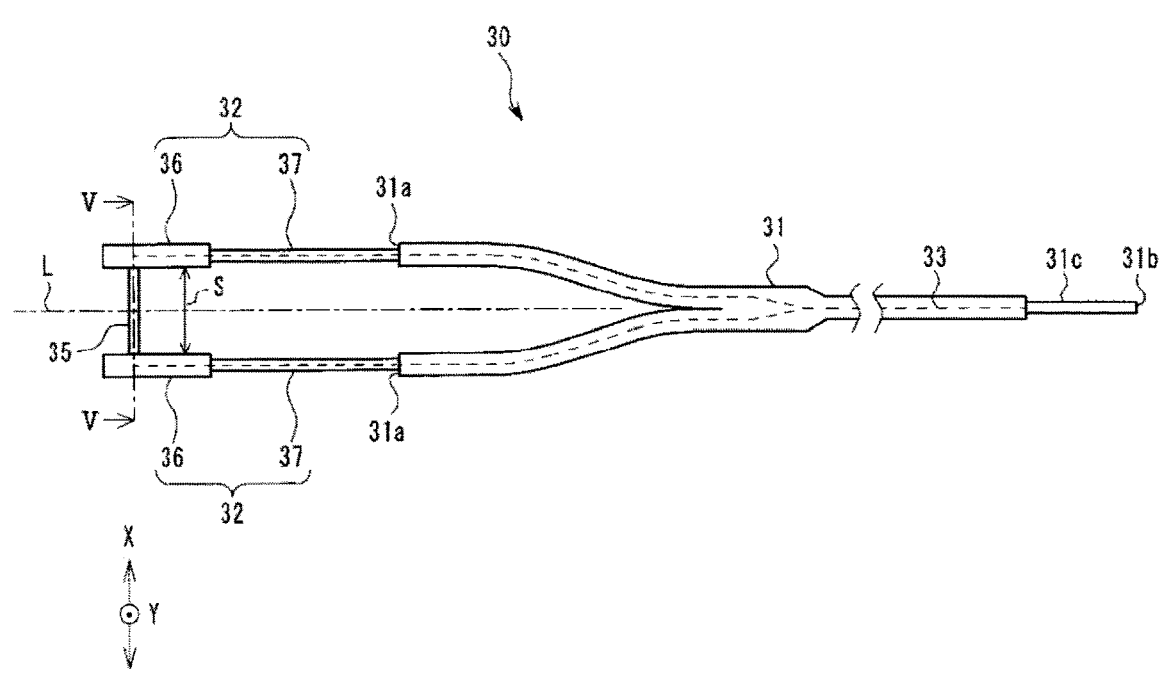
FIG. 3 is a diagram showing the electrode unit of the first embodiment seen along a second axis.
Figure 4:
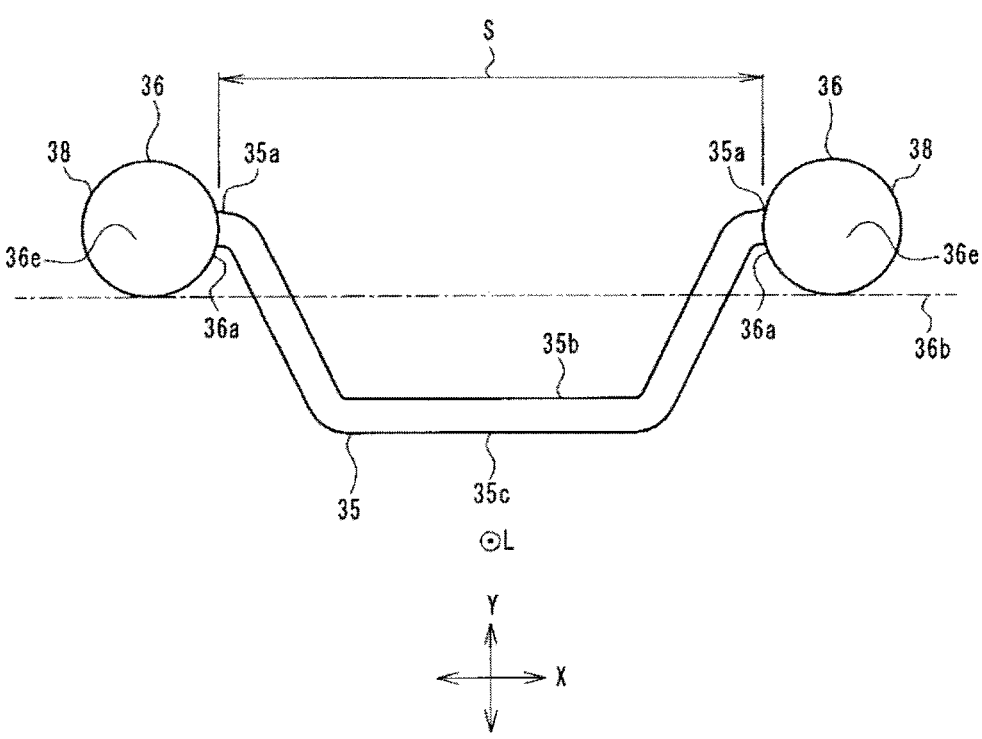
FIG. 4 is a diagram showing the electrode unit of the first embodiment seen from a distal end side along a longitudinal axis.
Figure 5:
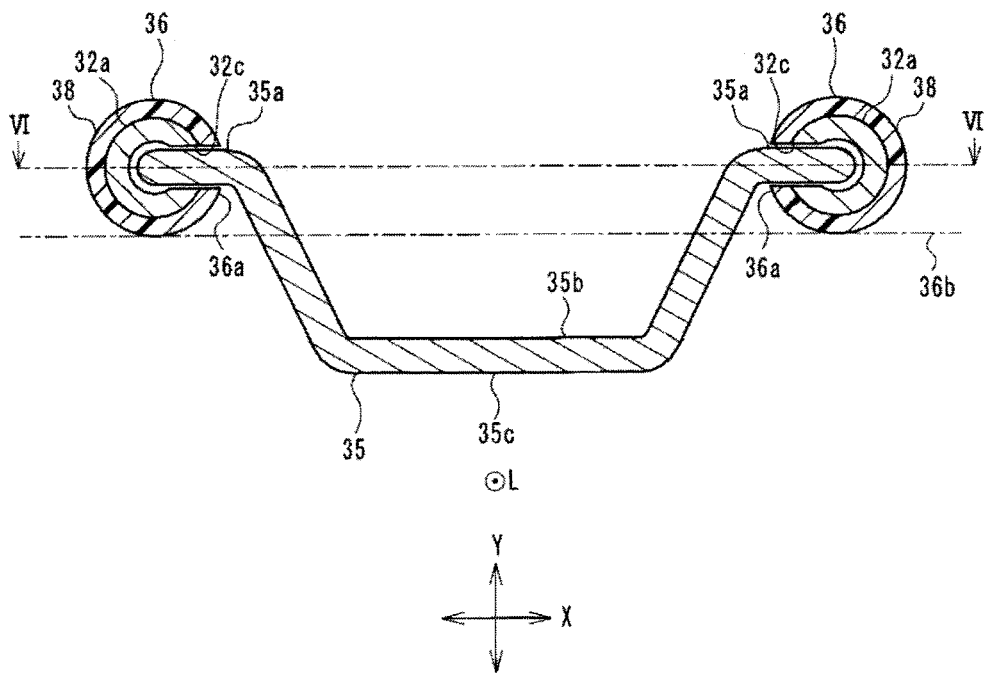
FIG. 5 is a cross-sectional view taken along a line V-V in FIG. 3.
Figure 6:
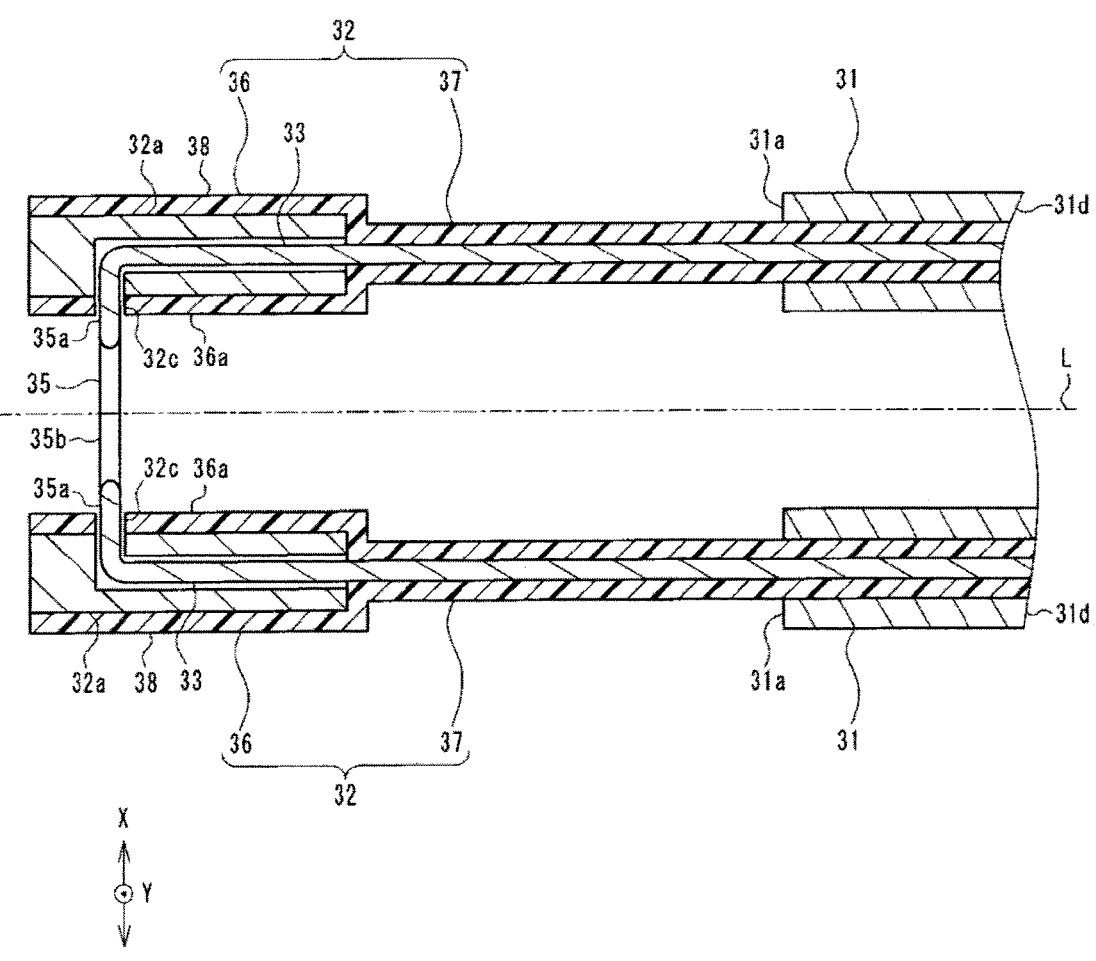
FIG. 6 is a cross-sectional view taken along a line VI-VI in FIG. 5.

FIG. 2 is a diagram showing the electrode unit 30 seen from left along the first axis X. In FIG. 2, an upper side of the diagram is the upper side. FIG. 3 is a diagram showing the electrode unit 30 seen from below along the second axis Y. In FIG. 3, an upper side of the diagram is the left side. FIG. 4 is a diagram showing the electrode unit 30 seen from the distal end side along the longitudinal axis L. FIG. 5 is a cross-sectional view taken along a line V-V in FIG. 3. In FIG. 4 and FIG. 5, an upper side of the diagrams is the upper side, and a right side of the diagrams is the left side. FIG. 6 is a cross-sectional view taken along a line VI-VI in FIG. 5. In FIG. 6, an upper side of the diagram is the right side.

As shown in FIG. 2 and FIG. 3, the electrode unit 30 has an elongated shape a longitudinal direction of which is a direction along the longitudinal axis L. The electrode unit 30 includes a proximal end rigid portion (proximal end rigid member) 31, an electrode supporting portion (electrode supporting member) 32, and the electrode 35.

The proximal end rigid portion 31 is an area fixed to the electrode unit holding portion 23 of the resectoscope 10. The electrode supporting portion 32 described later is joined to a distal end 31*a* of the proximal end rigid portion 31. An electrical connection portion 31*c* is provided on a proximal end 31*b* of the proximal end rigid portion 31. The electrical connection portion 31*c* is electrically connected to the electrode connector 24 of the resectoscope 10 in a state in which the proximal end rigid portion 31 is fixed to the electrode unit holding portion 23. The electrical connection portion 31*c* is electrically connected to the electrode 35 via an electrically conductive wire 33 inserted into the electrode unit 30.

The electrode supporting portion 32 supports the electrode 35. The electrode supporting portion 32 is an area protruding from the distal end 11*a* of the sheath 11 during use of the resectoscope 10. The electrode supporting portion 32 includes one or two distal end rigid portions (digital end rigid members) 36 and one or two elastic regions (elastic region members) 37. The electrode 35 is fixed to the distal end rigid portion 36.

The elastic region 37 joins a proximal end of the distal end rigid portion 36 with a distal end of the proximal end rigid portion 31. The bending rigidity of the elastic region 37 is lower than the bending rigidity of the distal end rigid portion 36 and the proximal end rigid portion 31.

The electrode 35 includes an electrically conductive linear member such as a metal wire. The electrode 35 protrudes from a surface of the distal end rigid portion 36.

The electrode 35 has a loop shape protruding from one point on the surface of the distal end rigid portion 36 to the outside of the distal end rigid portion 36, and entering from the other point to the inside of the distal end rigid portion 36. More specifically, the electrode 35 includes, in two points spaced apart from each other on the surface of the distal end rigid portion 36, a pair of base portions 35*a* supported by the distal end rigid portion 36 and an installation portion 35*b* connecting the pair of base portions 35*a* in a state of being spaced apart from the surface of the distal end rigid portion 36.

As shown in FIG. 4 and FIG. 5, the installation portion 35*b* is substantially angled-U shaped or substantially U shaped when seen in a direction along the longitudinal axis L. When seen in the direction along the first axis X, an apex portion 35*c* of the installation portion 35*b* protrudes from the base portion 35*a* in a direction intersecting the longitudinal axis L.

The pair of base portions 35*a* is electrically connected to the wire 33 inside the distal end rigid portion 36. As shown in FIG. 5 and FIG. 6, in the present embodiment, the wire 33 and the electrode 35 are configured with the same metallic linear member, as an example.

More specifically, the electrode supporting portion 32 of the present embodiment is provided with two distal end rigid portions 36. Each of the distal end rigid portions 36 has a columnar external shape a longitudinal direction of which is a direction along the longitudinal direction L. Note that, a cross-section of the distal end rigid portion 36 in the present embodiment illustrated in the drawings is substantially round. However, a cross-section of the distal end rigid portion 36 may also be either a parallelogram shape or other polygonal shapes.

The two distal end rigid portions 36 are arranged in substantially the same position in the direction along the longitudinal direction L, and arranged to be spaced apart from each other in the direction along the first axis X (lateral direction). In other words, the two distal end rigid portions 36 are arranged such that an overlapping part exists when seen in the direction along the first axis X. Therefore, the two distal end rigid portions 36 respectively have opposed faces 36*a* facing each other in the direction along the first axis X.

Note that "faces facing each other" as used herein refers to a surface oriented substantially to the left side of the distal end rigid portion 36 arranged on the right side, and a surface oriented substantially to the right side of the distal end rigid portion 36 arranged on the left side. In other words, the opposed faces 36*a* are areas facing a space sandwiched by the two distal end rigid portions 36. Therefore, the opposed faces 36*a* of the two distal end rigid portions 36 are not required to have respective areas parallel to each other.

The pair of base portions 35*a* of the electrode 35 are arranged respectively on the two distal end rigid portions 36. In other words, the electrode 35 is the metal wire 33 installing the two distal end rigid portions 36.

The pair of base portions 35a are arranged to protrude along the first axis X, respectively from the opposed faces 36a of the two distal end rigid portions 36. The pair of base portions 35a are arranged in substantially the same position in the direction along the longitudinal axis L. In other words, the pair of base portions 35a protrude respectively from the pair of opposed faces 36a along the first axis X, toward each other.

The installation portion 35b connects distal end portions of the pair of base portions 35a. The installation portion 35b is curved in a downward convex shape from the pair of base portions 35a, when seen in the direction along the longitudinal axis L. As shown in FIG. 4 and FIG. 5, the apex portion 35c of the installation portion 35b is positioned on the lower side of a lower end face 36b, facing the lower side, of the two distal end rigid portions 36.

The electrode 35 having the configuration described in the foregoing is exposed to the outside only within a space S between the two distal end rigid portions 36 when seen in the direction along the second axis Y, as shown in FIG. 3. In other words, an area of the electrode 35 exposed to the outside is arranged not to overlap the two distal end rigid portions 36 when seen in the direction along the second axis Y. The electrode 35 is exposed to the outside only within the space S between the two distal end rigid portions 36 when seen from the distal end side along the longitudinal axis L, as shown in FIG. 4. In other words, the area of the electrode 35 exposed to the outside is arranged not to overlap distal end faces 36e of the two distal end rigid portions 36.

As shown in FIG. 5 and FIG. 6, each of the distal end rigid portions 36 is configured with a ceramic pipe 32a and a covering portion 38. The ceramic pipe 32a and the covering portion 38 have electrically insulating properties. The ceramic pipe 32a is a hollow member into which the wire 33 is inserted. The covering portion 38 is a tube made of resin and covers the ceramic pipe 32a. On respective lateral faces of the ceramic pipe 32a and the covering portion 38, a through hole 32c that holds the base portion 35a of the electrode 35 is formed.

The electrode supporting portion 32 of the present embodiment is provided with two elastic regions 37, as an example. The two elastic regions 37 are connected respectively to the proximal ends of the two distal end rigid portions 36. Note that the electrode supporting portion 32 may also be configured to have one elastic region 37 connected to the proximal ends of both of the two distal end rigid portions 36.

The elastic region 37 of the present embodiment is configured of the covering portion 38, which is a tube made of resin. In the present embodiment, the covering portion 38 of the distal end rigid portion 36 and the covering portion 38 of the elastic region 37 are the same member continuous in the direction along the longitudinal axis L, as an example. The wire 33 is inserted into the covering portion 38 of the elastic region 37. In other words, in the present embodiment, the ceramic pipe 32a inserted into the covering portion 38 plays a role in making the bending rigidity of the distal end rigid portions 36 higher than the bending rigidity of the elastic region 37.

The proximal end rigid portion 31 of the present embodiment is configured of the covering portion 38, which is a tube made of resin, and a metal pipe 31d. In the present embodiment, the covering portion 38 of the proximal end rigid portion 31 and the covering portion 38 of the elastic region 37 are the same member continuous in the direction along the longitudinal axis L, as an example. The wire 33 is inserted into the covering portion 38 of the proximal end rigid portion 31. The metal pipe 31d covers the outer periphery of the covering portion 38. In other words, in the present embodiment, the metal pipe 31d plays a role in making the bending rigidity of the proximal end rigid portions 31 higher than the bending rigidity of the elastic region 37.

Note that a method for making the bending rigidity of the elastic region 37 lower than the bending rigidity of the distal end rigid portion 36 and the proximal end rigid portions 31 is not limited to the method of differentiating the material of constitutive members as in the present embodiment. For example, an external diameter of the elastic region 37 may be made smaller than an external diameter of the distal end rigid portion 36 and the proximal end rigid portions 31, to make the bending rigidity of the elastic region 37 lower than the bending rigidity of the distal end rigid portion 36 and the proximal end rigid portions 31.

Figure 7:
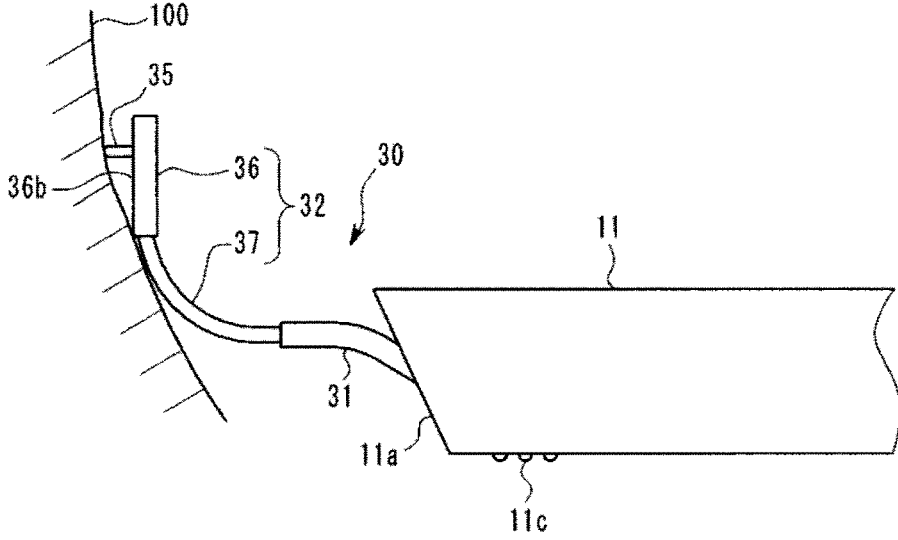
FIG. 7 is a diagram showing a first method of resecting tissue by using the electrode unit of the first embodiment.
Figure 8:
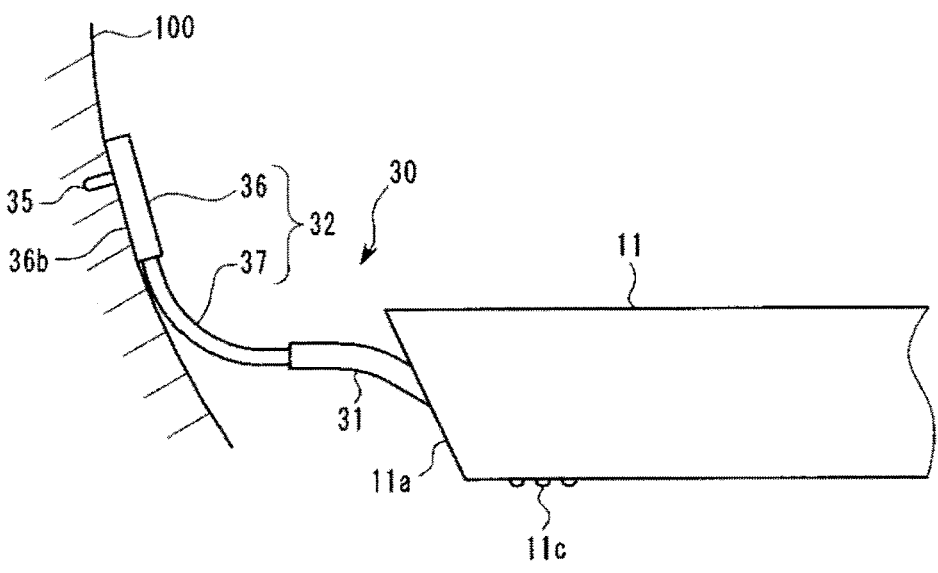
FIG. 8 is a diagram showing the first method of resecting tissue by using the electrode unit of the first embodiment.
Figure 9:
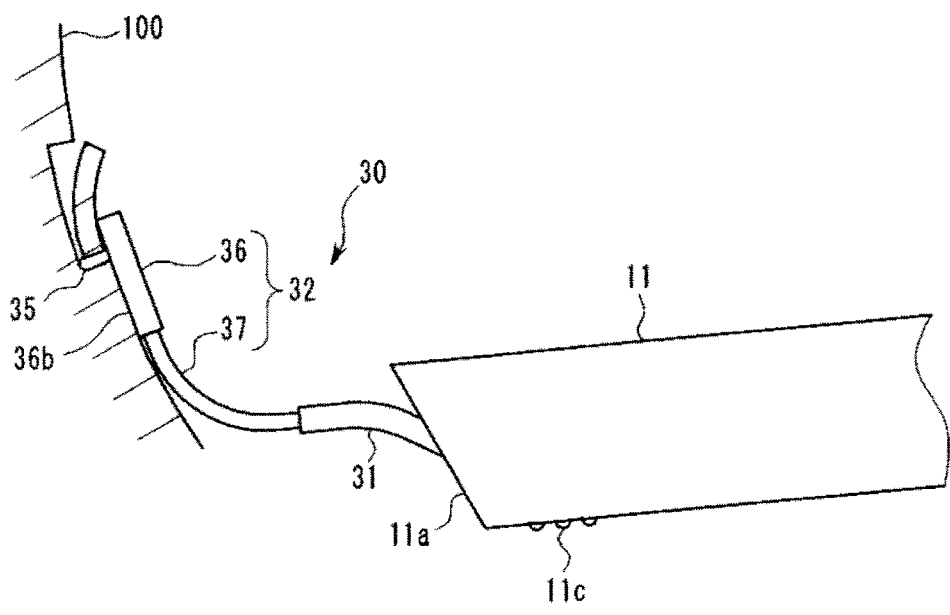
FIG. 9 is a diagram showing the first method of resecting tissue by using the electrode unit of the first embodiment.

A first method of resecting tissue in an organ 100 in the subject by using the electrode unit 30 and the endoscope system 1 of the present embodiment is described with reference to FIG. 7, FIG. 8, and FIG. 9. FIG. 7, FIG. 8, and FIG. 9 are diagrams schematically showing the inside of the organ 100.

In the case of resecting tissue inside the organ 100 by using the electrode unit 30, a user first orients the electrode supporting portion 32 such that the lower end face 36b of the distal end rigid portion 36 faces the tissue inside the organ 100. And then the user brings the electrode supporting portion 32 into contact with a wall surface of the organ 100 such that the electrode 35 protruding from the lower end face 36b of the distal end rigid portion 36 is in contact with the tissue, as shown in FIG. 7. Note that the method of inserting the electrode unit 30 and the sheath 11 of the resectoscope 10 into the organ 100 as well as the method of filling the organ 100 with the perfusate are the same as the method in the case of the conventional electrode unit, and therefore description of the methods is omitted.

Next, the user operates the switch 55a to start output of the high-frequency current from the high-frequency power control device 55. As a result, the high-frequency current flows from the electrode 35 to the collection electrode 11c through the perfusate, whereby the tissue in contact with the electrode 35 generates heat and is cut off. When the tissue is resected due to the start of output of the high-frequency current, the electrode 35 enters the tissue as shown in FIG. 8.

As described above, the electrode 35 is arranged not to overlap the distal end rigid portions 36 when seen in the direction along the second axis Y (from the lower side). Therefore, when the electrode 35 enters the tissue to a predetermined depth, the distal end rigid portion 36 comes into contact with tissue not being cut off by the electrode 35. In other words, the lower end face 36b of the distal end rigid portion 36 functions as a stopper configured to restrict the depth by which the electrode 35 enters the tissue.

If, unlike the present embodiment, the electrode 35 was arranged to overlap the lower end face 36b of the distal end rigid portion 36 when seen from the lower side, the lower end face 36b would be pressed against the tissue cut off by the electrode 35. In this case, the force of the lower end face 36b restricting the proceeding of the electrode 35 into the tissue may be weaker than in the present embodiment. The present embodiment can avoid such a state, and enables reliable restriction of the depth by which the electrode 35 enters the tissue.

Therefore, in the present embodiment, even when the force with which the user presses the electrode supporting portion 32 against the wall surface of the organ 100 varies, the electrode 35 can be prevented from further entering the tissue, from the state in which the distal end rigid portions 36 is in contact with the tissue.

As shown in FIG. 9, the user moves the resectoscope 10 to move the electrode supporting portion 32 along the wall surface of the organ 100. As a result, the electrode 35 moves in a direction along the wall surface inside the tissue, whereby a tissue piece of a predetermined thickness is resected.

As described above, even when the force with which the user presses the electrode supporting portion 32 against the wall surface of the organ 100 varies, the depth by which the electrode 35 enters the tissue is kept constant. Also, even when the force with which the user presses the resectoscope 10 in a tissue direction varies, the elastic region 37 bends, whereby the change in the force of pressing the electrode 35 in the tissue direction is kept substantially constant. As a result, an amount of the tissue to be deformed by the distal end rigid portions 36 is also kept substantially constant, whereby the depth by which the electrode 35 enters the tissue is also kept substantially constant. In the present embodiment, even when movement of the resectoscope 10 by the user does not follow the shape of the wall surface of the organ 100 and a distance between the wall surface of the organ 100 and the distal end 11a of the sheath 11 varies, the elastic region 37 elastically deforms to keep the state in which the distal end rigid portions 36 is in contact with the tissue. As described above, when the distal end rigid portions 36 is in contact with the tissue, the depth by which the electrode 35 enters the tissue is kept constant.

Next, a second method of resecting tissue in an organ 100 in a subject by using the electrode unit 30 and the endoscope system 1 of the present embodiment is described with reference to FIG. 10, FIG. 11, and FIG. 12.

Figure 10:
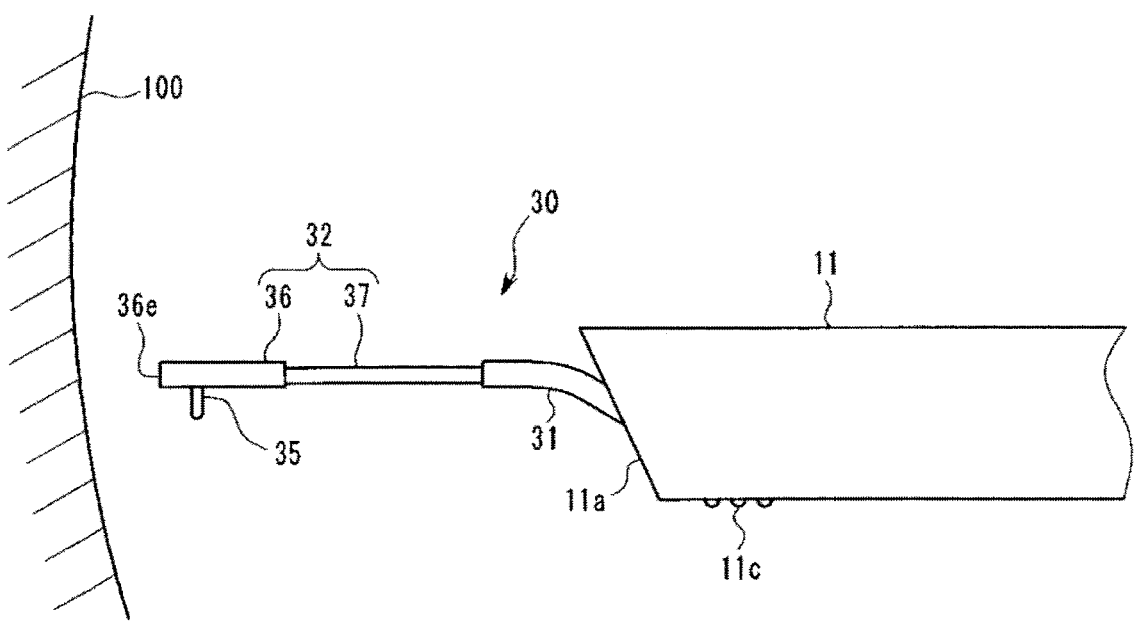
FIG. 10 is a diagram showing a second method of resecting tissue by using the electrode unit of the first embodiment.

In the second method, as shown in FIG. 10, the user orients the electrode supporting portion 32 such that the distal end face 36e of the distal end rigid portion 36 faces the tissue to be resected in the organ 100. At this moment, the electrode unit 30 is not in contact with the tissue to be resected and the vicinity of the tissue to be resected. Next, in the state in which the electrode unit 30 is not in contact with the tissue to be resected and the vicinity of the tissue to be resected, the user operates the switch 55a to start output of the high-frequency current from the high-frequency power control device 55.

Figure 11:
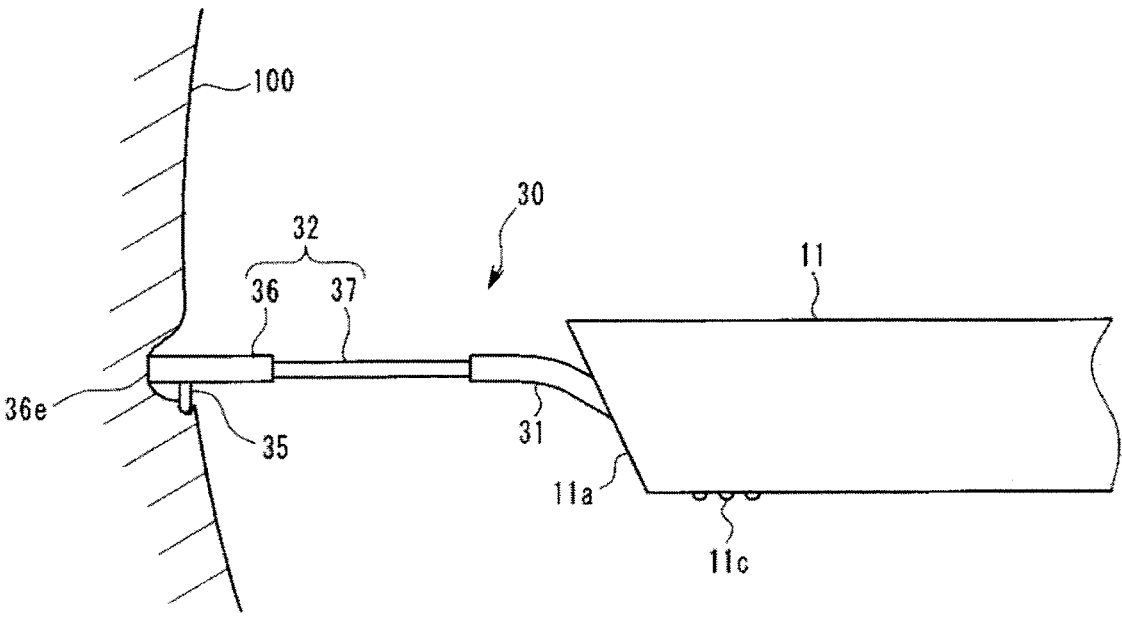
FIG. 11 is a diagram showing the second method of resecting tissue by using the electrode unit of the first embodiment.

Next, the user moves the electrode unit 30 toward the distal end side to bring the distal end face 36e of the distal end rigid portion 36 into contact with the wall surface of the organ 100 as shown in FIG. 11. As described above, the electrode 35 is arranged in such a position not to overlap the distal end face 36e when seen in the direction along the longitudinal axis L. Therefore, in this operation, movement of the electrode unit 30 toward the distal end side is stopped when the distal end face 36e comes into contact with the wall surface of the organ 100. In other words, the distal end face 36e of the distal end rigid portion 36 functions as a stopper configured to restrict the depth by which the electrode 35 enters the tissue.

In a phase shown in FIG. 11, when the electrode 35 is in contact with the tissue, the electrode 35 is contact with the tissue in a position different from the position where the distal end face 36e is in contact with the tissue. Therefore, in the phase shown in FIG. 11, even when the electrode 35 cuts off the tissue, the distal end rigid portion 36 is in contact with the tissue not being cut off by the electrode, whereby the distal end face 36e of the distal end rigid portion 36 functions as a stopper.

Figure 12:
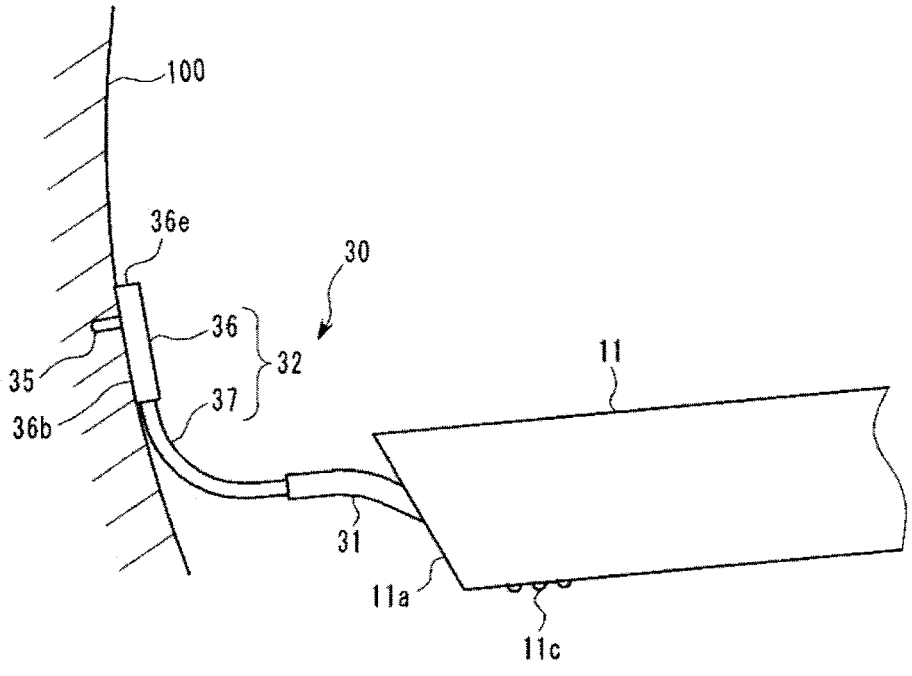
FIG. 12 is a diagram showing the second method of resecting tissue by using the electrode unit of the first embodiment.

Next, the user moves the electrode supporting portion 32 downward while the distal end face 36e is in contact with the wall surface of the organ 100, to bring the lower end face 36b of the distal end rigid portion 36 into contact with the tissue as shown in FIG. 12. This operation curves the elastic region 37. In a phase shown in FIG. 12, the lower end face 36b of the distal end rigid portions 36 functions as the stopper configured to restrict the depth by which the electrode 35 enters the tissue, in a similar manner to the first method. Therefore, also in the case of employing the second method, the depth by which the electrode 35 enters the tissue can be kept constant, in a similar manner to the first method.

Next, as shown in FIG. 9, the user moves the resectoscope 10 to move the electrode supporting portion 32 along the wall surface of the organ 100, in a similar manner to the first method. As a result, the loop electrode 35 moves in a direction along the wall surface inside the tissue, whereby a tissue piece of a predetermined thickness is resected.

As explained in the foregoing, the electrode unit 30 and the endoscope system 1 of the present embodiment can keep constant the depth by which the electrode 35 enters the tissue, even when a trajectory of the electrode 35 moved by the user staggers, or when the force applied by the user to the electrode 35 varies. Therefore, the electrode unit 30 and the endoscope system 1 of the present embodiment facilitate control of the thickness of the resected tissue.

Note that configurations of the electrode supporting portion 32 and the electrode 35 provided in the electrode unit 30 are not limited to the configurations of the present embodiment.

Figure 13:
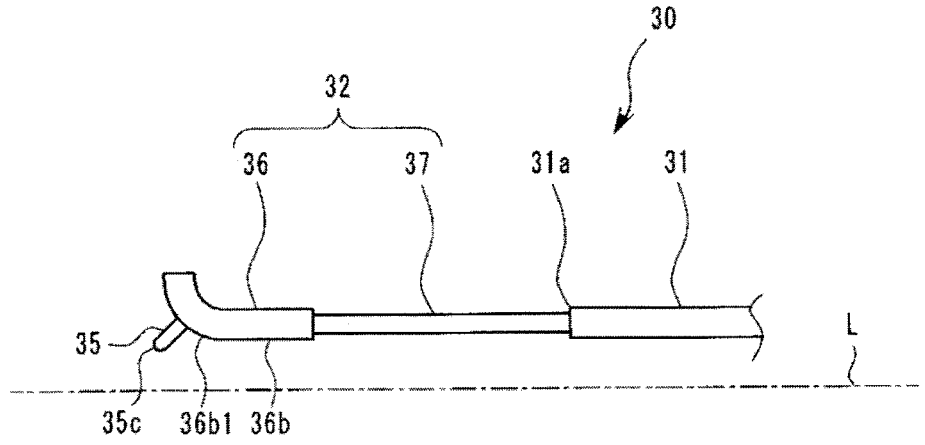
FIG. 13 is a diagram showing a first modification of the electrode unit of the first embodiment seen along a first axis.
Figure 13:
Figure 14:
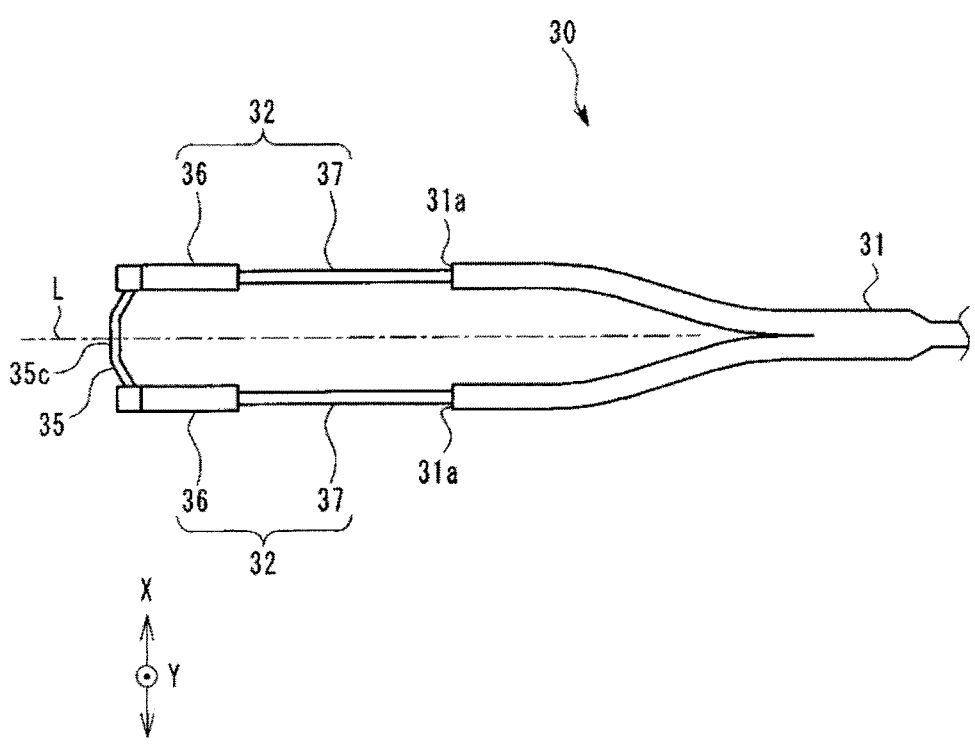
FIG. 14 is a diagram showing the first modification of the electrode unit of the first embodiment seen along a second axis.
Figure 15:
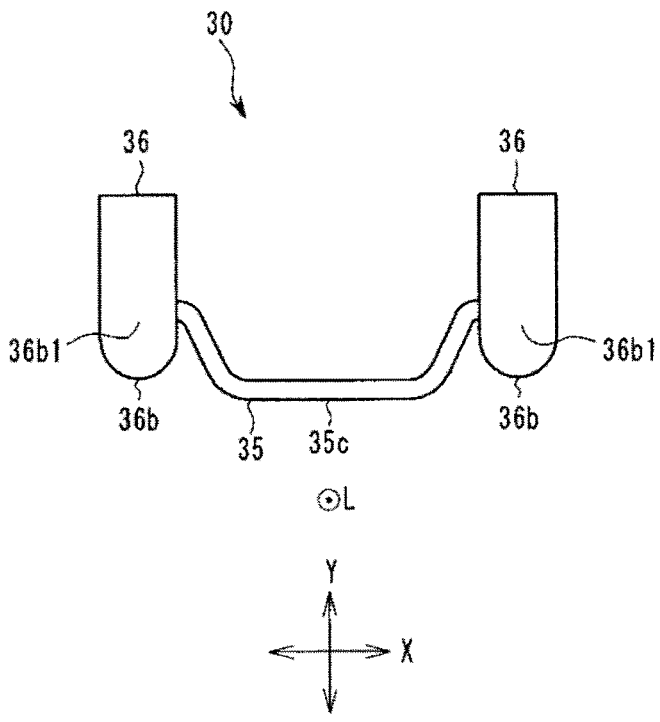
FIG. 15 is a diagram showing the first modification of the electrode unit of the first embodiment seen from the distal end side along the longitudinal axis.

FIG. 13, FIG. 14, and FIG. 15 show a first modification of the electrode unit 30. In the electrode unit 30 of the first modification, the lower end face 36b of the distal end rigid portion 36 has a curved shape when seen in the direction along the first axis X.

A curved face portion 36b1 that is curved upward as getting closer to the distal end side when seen in the direction along the first axis X is formed on the lower end face 36b of the distal end rigid portion 36 of the first modification. When seen in the direction along the first axis X, the electrode 35 protrudes in a direction substantially orthogonal to the curved face portion 36b1. More specifically, the electrode 35 protrudes downward toward the distal end side from the distal end rigid portion 36.

The electrode unit 30 of the first modification facilitates the operation of bringing the electrode 35 into contact with the tissue when the wall surface of the organ 100 is substantially orthogonal to the longitudinal axis L.

Figure 16:
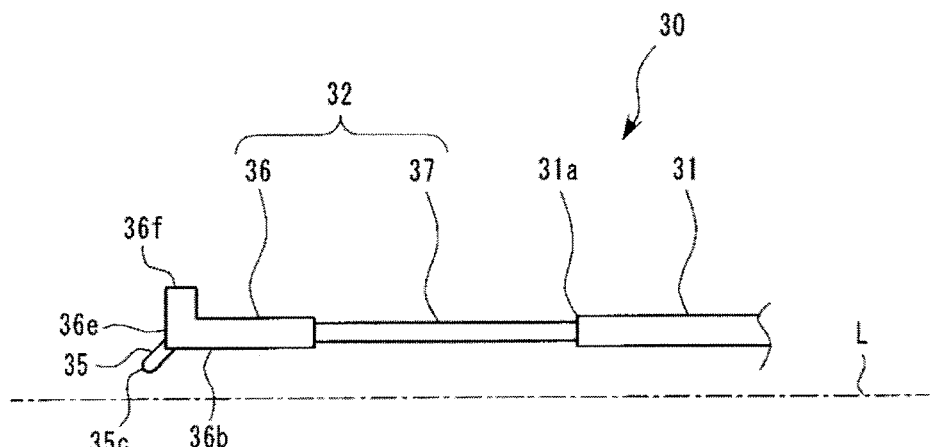
FIG. 16 is a diagram showing a second modification of the electrode unit of the first embodiment seen along the first axis.
Figure 16:
Figure 17:
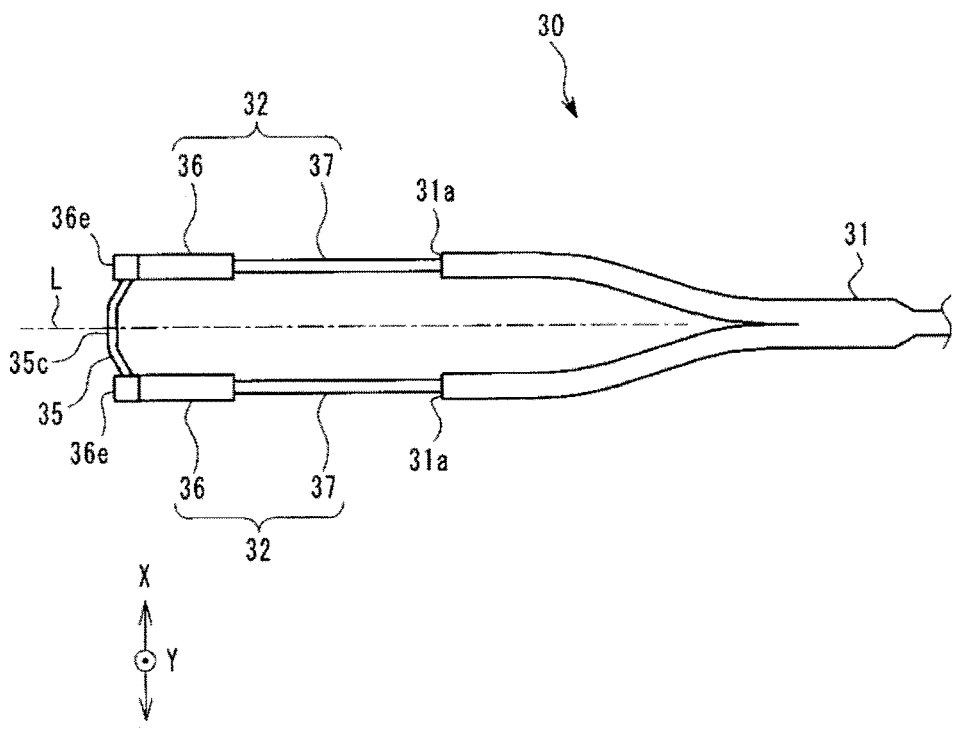
FIG. 17 is a diagram showing the second modification of the electrode unit of the first embodiment seen along the second axis.
Figure 18:
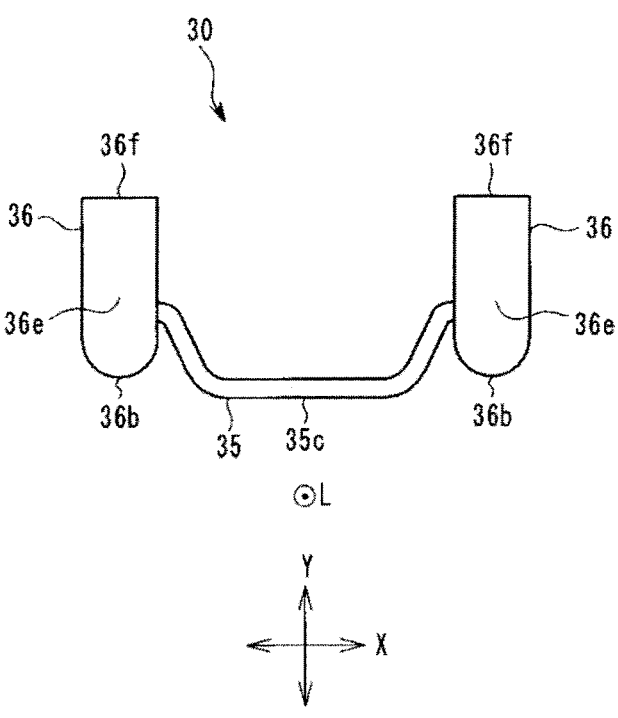
FIG. 18 is a diagram showing the second modification of the electrode unit of the first embodiment seen from the distal end side along the longitudinal axis.

FIG. 16, FIG. 17, and FIG. 18 show a second modification of the electrode unit 30. In the electrode unit 30 of the second modification, the apex portion 35c of the electrode 35 protrudes to the lower side of the lower end face 36b of the distal end rigid portion 36 and to the distal end side of the distal end face 36e of the distal end rigid portion 36.

The electrode unit 30 of the first modification enables resection of the tissue, through pressing any one of the lower end face 36b and the distal end face 36e against the wall surface of the organ 100 to bring the electrode 35 into contact with the tissue.

The distal end rigid portion 36 of the second modification is provided with a convex portion 36f. The convex portion 36f protrudes in a direction different from the electrode 35. More specifically, the convex portion 36f protrudes upward along the second axis Y from the distal end of the distal end rigid portion 36. A face on the distal end side of the convex portion 36*f* is the same face as the distal end face 36*e*. Due to the convex portion 36*f* formed at the distal end of the distal end rigid portion 36, an area in contact with the wall surface of the organ 100 is increased, whereby, even when the force of pressing the electrode 35 against the tissue is great, a pressure applied to the tissue is distributed and variation is suppressed. As a result, an amount of the tissue to be deformed by the distal end rigid portions 36 is also kept substantially constant, whereby it is easy to keep constant the depth by which the electrode 35 enters the tissue.

Figure 19:
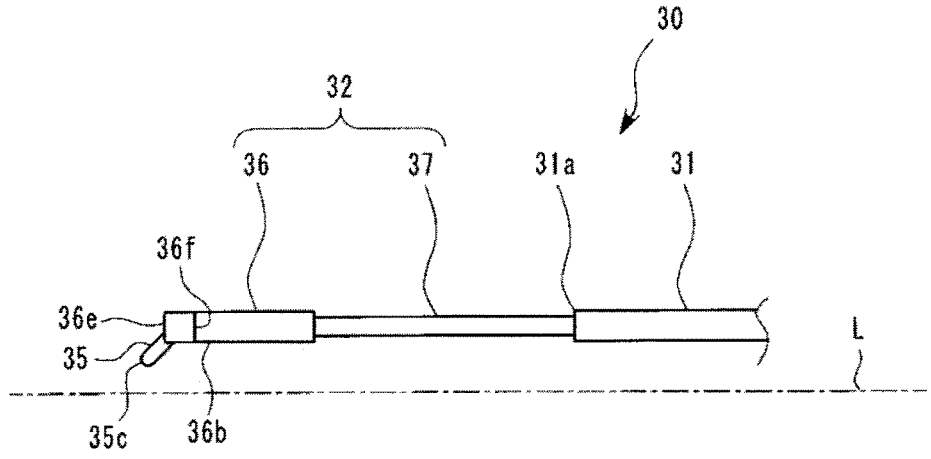
FIG. 19 is a diagram showing a third modification of the electrode unit of the first embodiment seen along the first axis.
Figure 19:
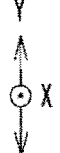
Figure 20:
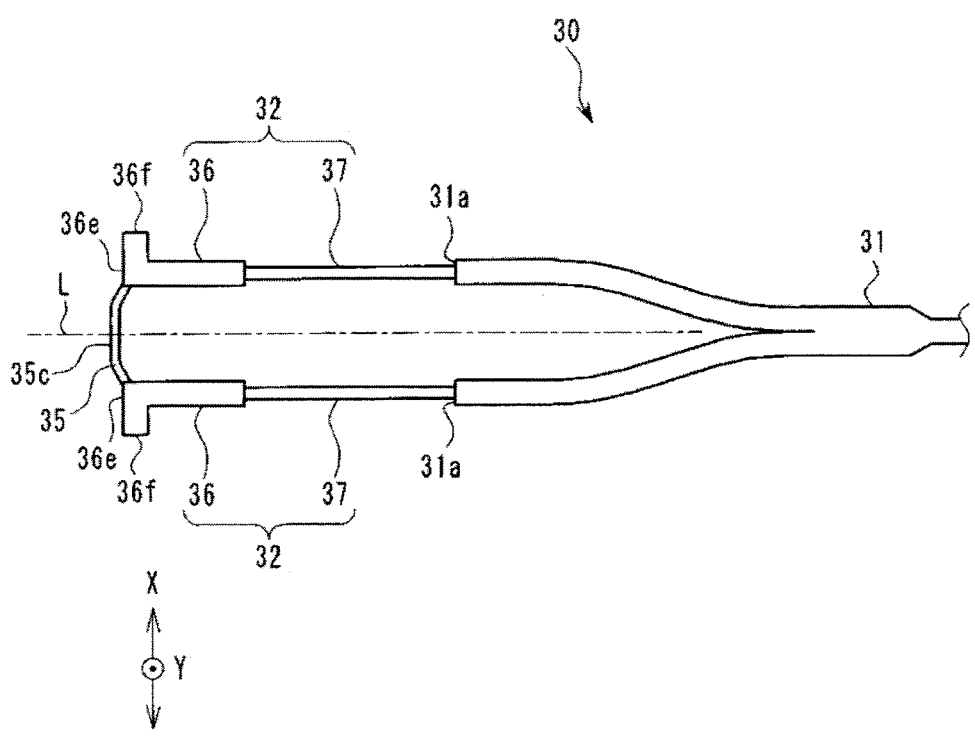
FIG. 20 is a diagram showing the third modification of the electrode unit of the first embodiment seen along the second axis.
Figure 21:
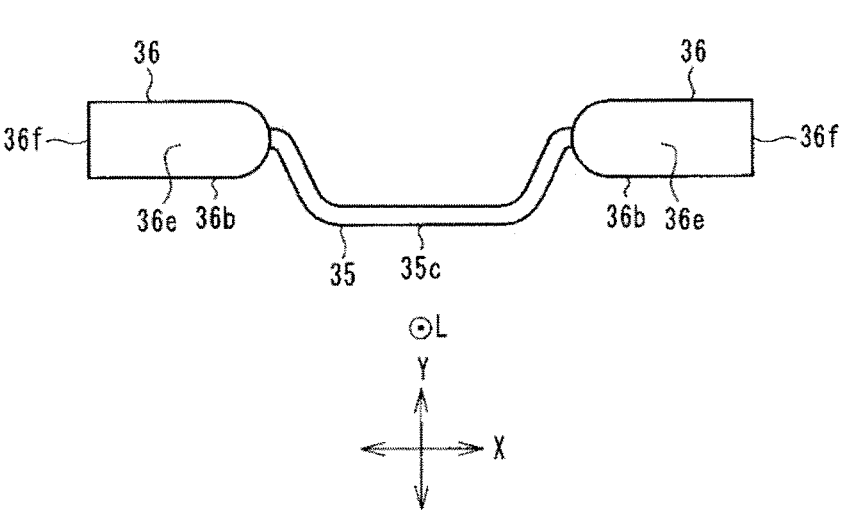
FIG. 21 is a diagram showing the third modification of the electrode unit of the first embodiment seen from the distal end side along the longitudinal axis.

FIG. 19, FIG. 20, and FIG. 21 show a third modification of the electrode unit 30. In the electrode unit 30 of the third modification, in a similar manner to the second modification, the apex portion 35*c* of the electrode 35 protrudes to the lower side of the lower end face 36*b* of the distal end rigid portion 36 and to the distal end side of the distal end face 36*e* of the distal end rigid portion 36.

The distal end rigid portions 36 of the third modification are provided with a pair of convex portions 36*f* protruding from the distal end in the lateral direction along the first axis X. In the third modification illustrated in the drawings, the pair of convex portions 36*f* protrude respectively from the pair of distal end rigid portions 36 in directions away from each other along the first axis X. Note that the pair of convex portions 36*f* may also protrude respectively from the pair of distal end rigid portions 36 in directions of getting closer to each other along the first axis X.

The electrode unit 30 of the third modification, in a similar manner to the second modification, enables resection of the tissue, through pressing any one of the lower end face 36*b* and the distal end face 36*e* against the wall surface of the organ 100 to bring the electrode 35 into contact with the tissue. Due to the convex portion 36*f* formed at the distal end of the distal end rigid portion 36, an area in contact with the wall surface of the organ 100 is increased, whereby it is easy to keep constant the depth by which the electrode 35 enters the tissue.

Figure 22:
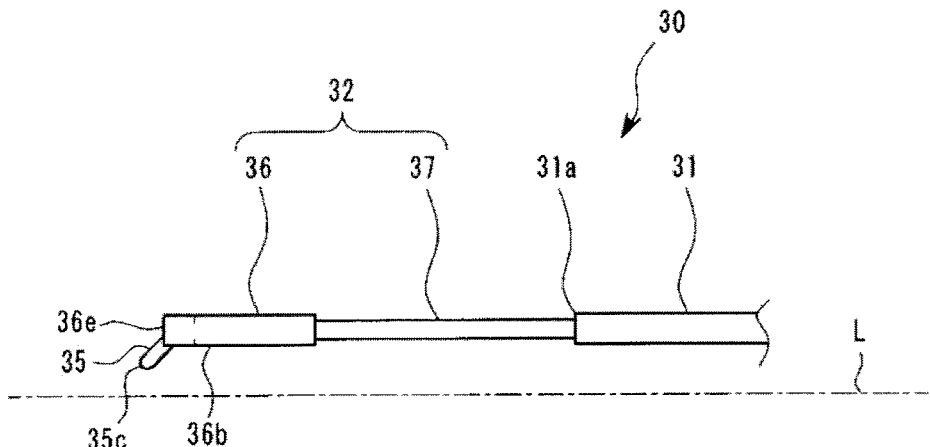
FIG. 22 is a diagram showing a fourth modification of the electrode unit of the first embodiment seen along the first axis.
Figure 23:
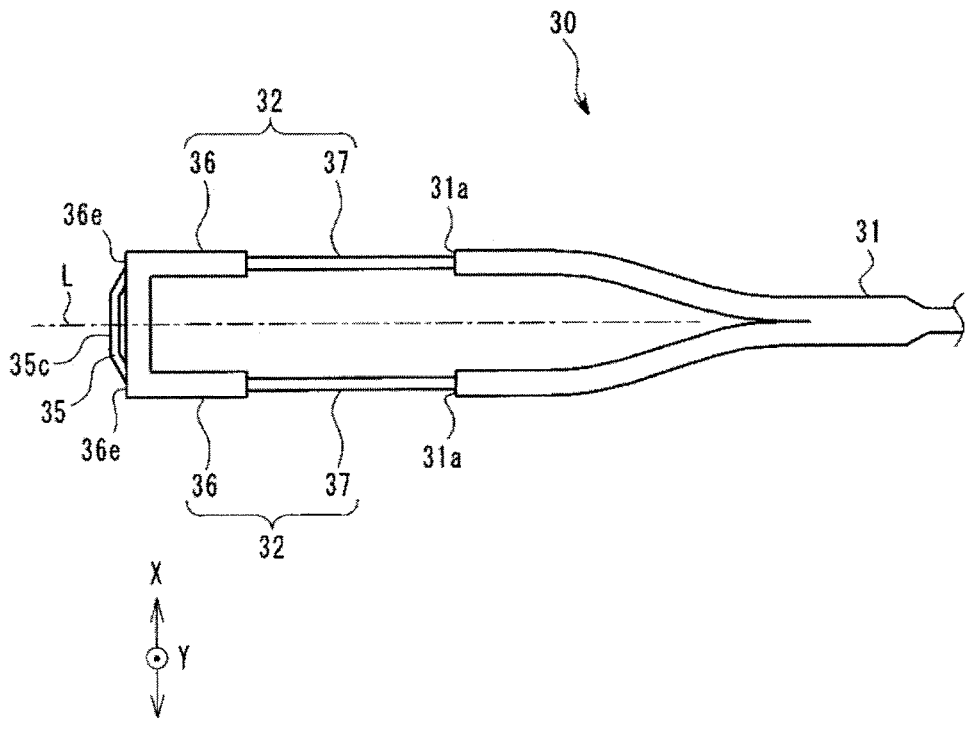
FIG. 23 is a diagram showing the fourth modification of the electrode unit of the first embodiment seen along the second axis.
Figure 24:
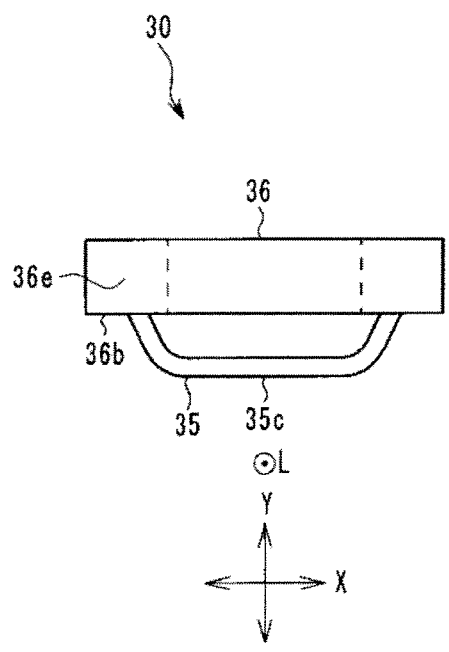
FIG. 24 is a diagram showing the fourth modification of the electrode unit of the first embodiment seen from the distal end side along the longitudinal axis.

FIG. 22, FIG. 23, and FIG. 24 show a fourth modification of the electrode unit 30. The electrode supporting portion 32 of the fourth modification is provided with one distal end rigid portion 36 and two elastic regions 37. The apex portion 35*c* of the electrode 35 protrudes to the lower side of the lower end face 36*b* of the distal end rigid portion 36 and to the distal end side of the distal end face 36*e* of the distal end rigid portion 36.

Figure 25:
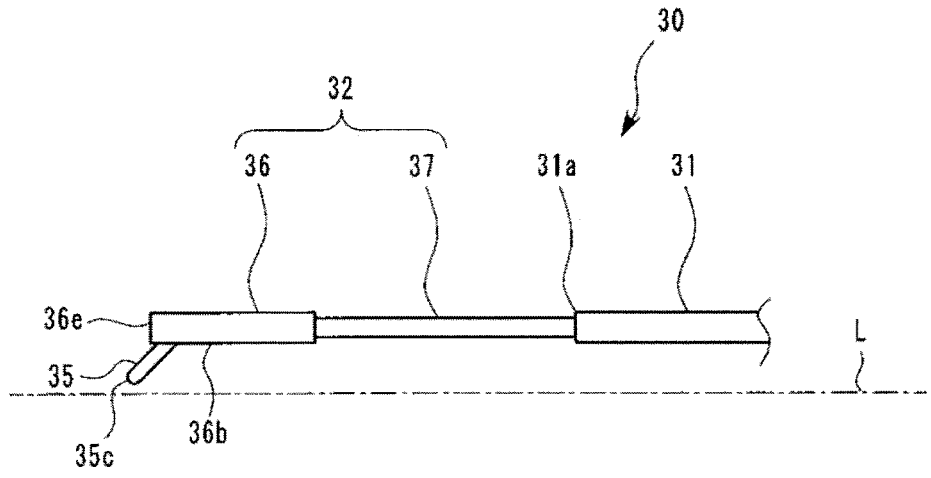
FIG. 25 is a diagram showing a fifth modification of the electrode unit of the first embodiment seen along the first axis.
Figure 25:
Figure 26:
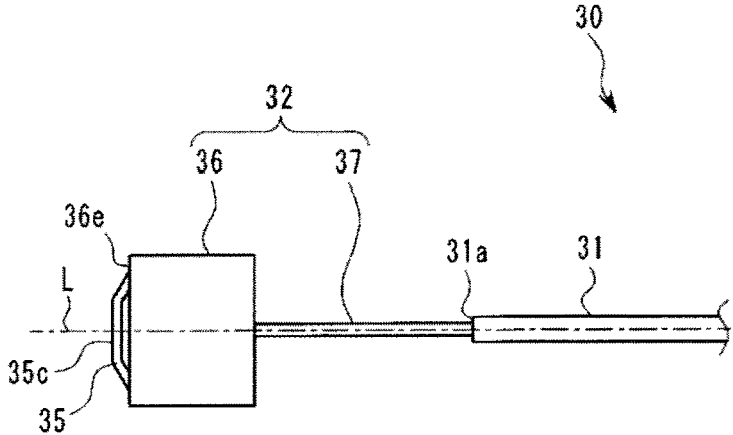
FIG. 26 is a diagram showing the fifth modification of the electrode unit of the first embodiment seen along the second axis.
Figure 26:
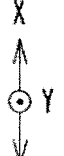
Figure 27:
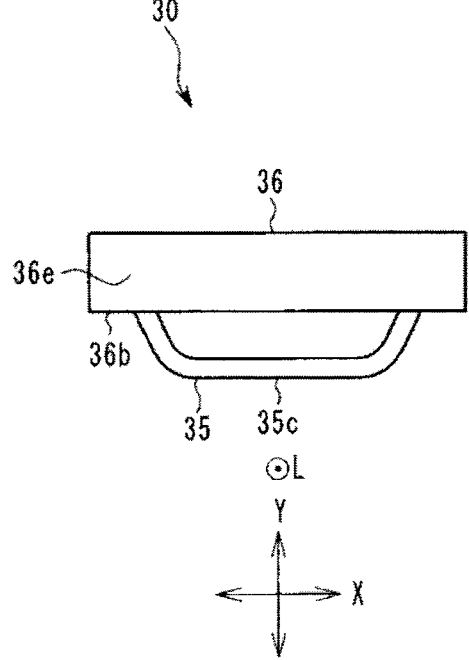
FIG. 27 is a diagram showing the fifth modification of the electrode unit of the first embodiment seen from the distal end side along the longitudinal axis.

FIG. 25, FIG. 26, and FIG. 27 show a fifth modification of the electrode unit 30. The electrode supporting portion 32 of the fifth modification is provided with one distal end rigid portion 36 and one elastic regions 37. The apex portion 35*c* of the electrode 35 protrudes to the lower side of the lower end face 36*b* of the distal end rigid portion 36 and to the distal end side of the distal end face 36*e* of the distal end rigid portion 36.

As shown in the fourth and the fifth modifications, the number of the distal end rigid portions 36 and the number of the elastic regions 37 included in the electrode supporting portion 32 may be either one or two.

Figure 28:
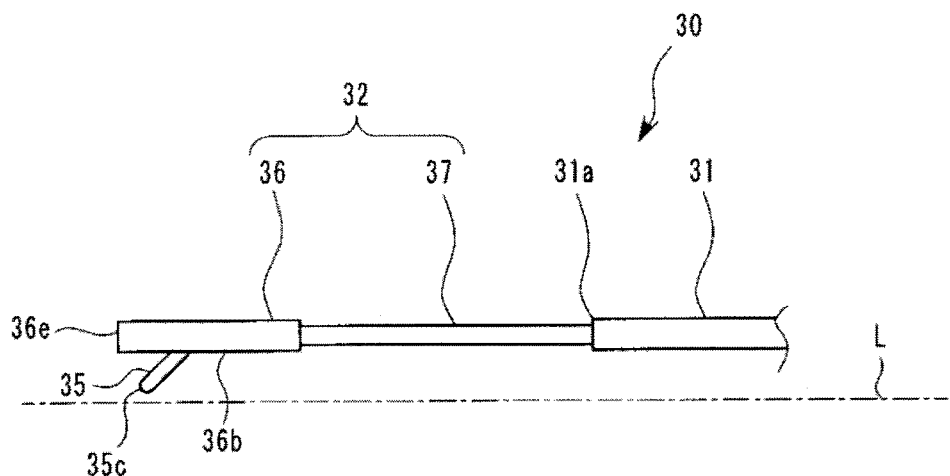
FIG. 28 is a diagram showing a sixth modification of the electrode unit of the first embodiment seen along the first axis.
Figure 28:
Figure 29:
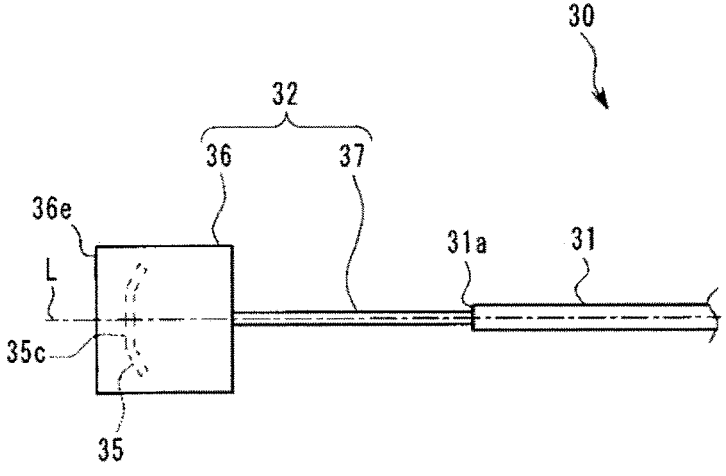
FIG. 29 is a diagram showing the sixth modification of the electrode unit of the first embodiment seen along the second axis.
Figure 29:
Figure 30:
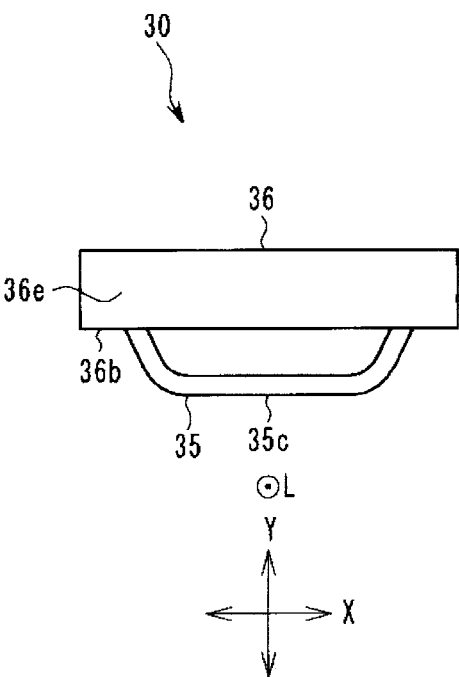
FIG. 30 is a diagram showing the sixth modification of the electrode unit of the first embodiment seen from the distal end side along the longitudinal axis.

FIG. 28, FIG. 29, and FIG. 30 show a sixth modification of the electrode unit 30. The electrode supporting portion 32 of the sixth modification is provided with one distal end rigid portion 36 and one elastic region 37. The apex portion 35*c* of the electrode 35 protrudes downward from the lower end face 36*b* of the distal end rigid portion 36. Unlike the fifth modification, the apex portion 35*c* of the electrode 35 is positioned on the proximal end side relative to the distal end face 36*e* of the distal end rigid portion 36.

Second Embodiment

Hereinafter, a second embodiment of the present invention is described. In the following description, only differences from the first embodiment are explained, and components similar to the components of the first embodiment are denoted by the same reference symbols and description of such components is omitted as appropriate.

Figure 31:
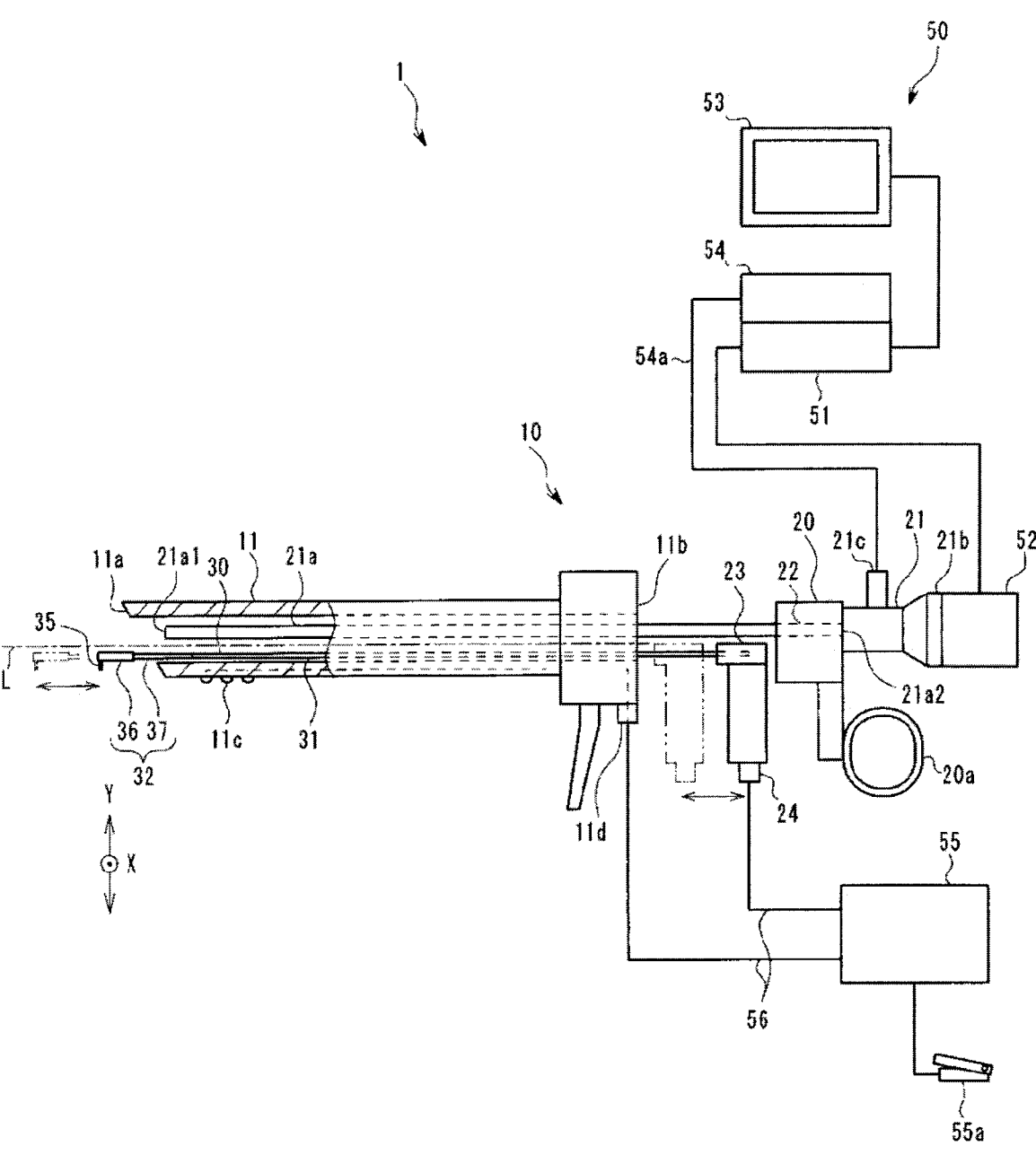
FIG. 31 is a diagram showing a schematic configuration of an endoscope system of a second embodiment.

FIG. 31 is a diagram showing a schematic configuration of an endoscope system 1 of the second embodiment. The endoscope system 1 of the present embodiment enables movement of the electrode unit 30 relative to the telescope 21 along the longitudinal axis L.

More specifically, in the endoscope system 1 of the present embodiment, the slider 20 and the electrode unit holding portion 23 are separated. The electrode unit holding portion 23 moves relative to the sheath 11 along the longitudinal axis L, independently of the slider 20. The electrode unit holding portion 23 is provided with the electrode connector 24.

In the endoscope system 1 of the present embodiment, only the electrode unit 30 can be moved relative to the sheath 11 along the longitudinal axis L while the position of the telescope 21 is fixed with respect to the sheath 11, by moving the electrode unit holding portion 23 relative to the sheath 11 along the longitudinal axis L.

In the endoscope system 1, a protrusion length of the elastic region 37 from the distal end 11*a* of the sheath 11 can be changed by moving the electrode unit 30 relative to the sheath 11 along the longitudinal axis L. A part of the elastic region 37 positioned on the proximal end side relative to the distal end 11*a* of the sheath 11 is surrounded by the sheath 11 and less likely to undergo curved deformation. Therefore, in the endoscope system 1 of the present embodiment, the length by which the elastic region 37 elastically deforms when the distal end rigid portion 36 is pressed against the wall surface of the organ 100 can be changed, through changing the protrusion length of the elastic region 37 from the distal end 11*a* of the sheath 11.

When the distal end rigid portion 36 is pressed against the wall surface of the organ 100 and the elastic region 37 elastically deforms, the distal end rigid portion 36 and the electrode 35 move upward within a field of view of the telescope 21. During this operation, the distal end rigid portion 36 and the electrode 35 may move to the outside of the field of view of the telescope 21. In this case, in the present embodiment, the distal end rigid portion 36 and the electrode 35 can be prevented from moving to the outside of the field of view of the telescope 21, by moving the electrode unit 30 to the proximal end side with respect to the sheath 11 to reduce the length by which the elastic region 37 elastically deforms.

Note that the configuration of the electrode supporting portion 32 of the electrode unit 30 of the present embodiment may be any one of the configurations of the first embodiment shown in FIG. 2 to FIG. 30 and the modifications of the first embodiment.

Third Embodiment

Hereinafter, a third embodiment of the present invention is described. In the following description, only differences from the first embodiment are explained, and components similar to the components of the first embodiment are denoted by the same reference symbols and description of such components is omitted as appropriate.

Figure 32:
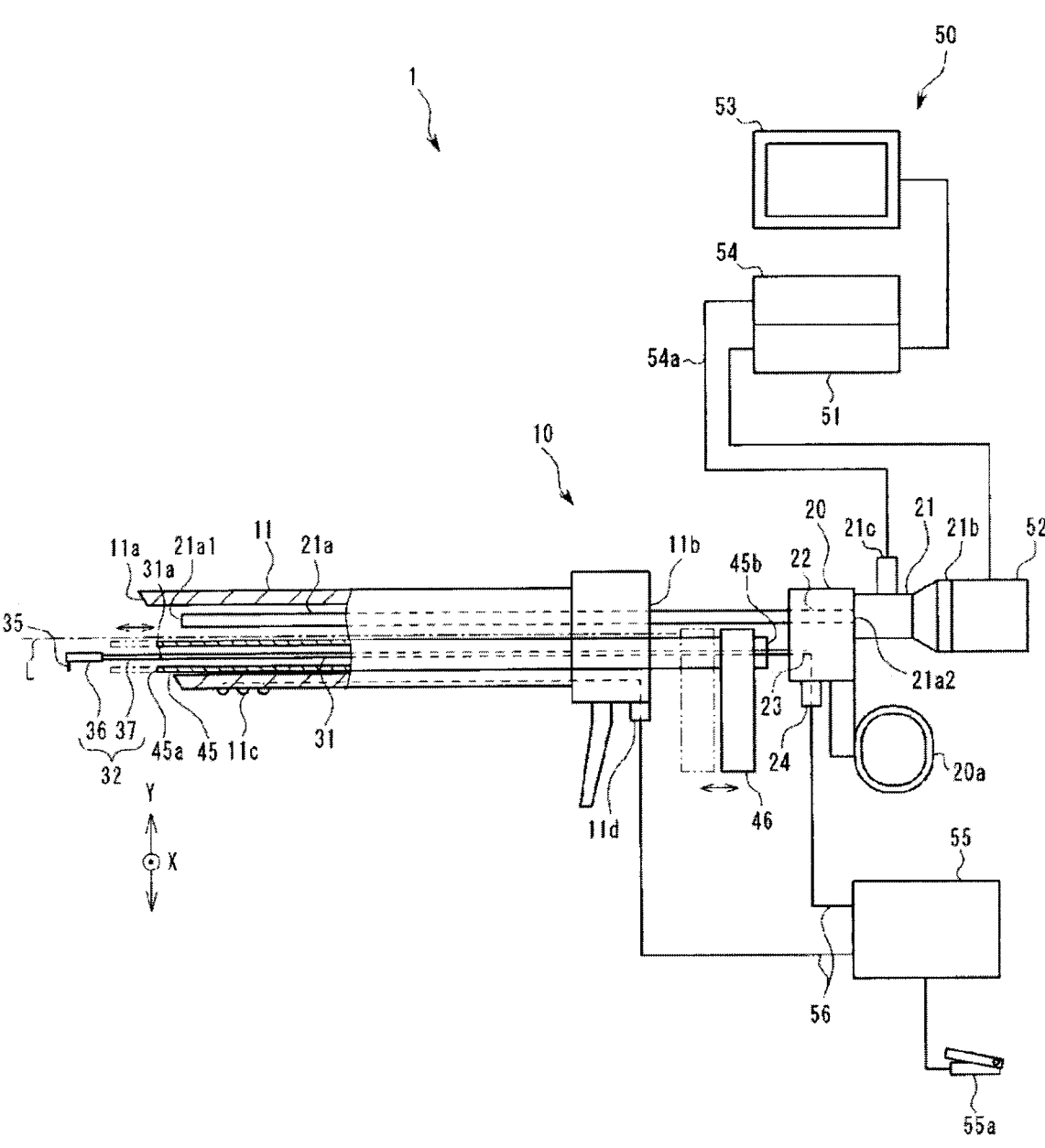
FIG. 32 is a diagram showing a schematic configuration of an endoscope system of a third embodiment.

FIG. 32 is a diagram showing a schematic configuration of an endoscope system 1 of the third embodiment. The endoscope system 1 of the present embodiment is different from the first embodiment in that the electrode unit 30 is provided with an electrode sheath 45 and an operation portion (operation member) 46.

The electrode sheath 45 is a tubular member having higher bending rigidity than the elastic region 37. The electrode sheath 45 is arranged to surround the outer periphery of the proximal end rigid portion 31. The electrode sheath 45 is movable relative to the proximal end rigid portion 31 along the longitudinal axis L.

In the state in which the electrode sheath 45 has moved to the distalmost side within a movable range with respect to the proximal end rigid portion 31, the distal end 45a of the electrode sheath 45 is positioned on the distal end side relative to the distal end 31a of the proximal end rigid portion 31. In the state in which the electrode sheath 45 has moved to the distalmost side within the movable range with respect to the proximal end rigid portion 31, a part or an entirety of the elastic region 37 is accommodated in the electrode sheath 45.

The proximal end 45b of the electrode sheath 45 protrudes on the proximal end side relative to the proximal end 11b of the sheath 11. The operation portion 46 is provided in an area of the electrode sheath 45 protruding on the proximal end side relative to the proximal end 11b of the sheath 11 of the electrode sheath 45. In the state in which the distal end 11a of the sheath 11 and the electrode supporting portion 32 of the electrode unit 30 are inserted into the subject, the operation portion 46 is positioned outside of the subject.

The operation portion [40] 46 is movable relative to the proximal end rigid portion 31 together with the electrode sheath 45. In other words, by moving the operation portion 46 relative to the proximal end rigid portion 31, the sheath 11 moves relative to the proximal end rigid portion 31. In the electrode unit 30 of the present embodiment, the protrusion length of the elastic region 37 from the distal end 45a of the electrode sheath 45 can be changed by moving the sheath 11 relative to the proximal end rigid portion 31. A part of the elastic region 37 surrounded by the electrode sheath 45 is less likely to undergo curved deformation. Therefore, in the electrode unit 30 of the present embodiment, the length by which the elastic region 37 elastically deforms when the distal end rigid portion 36 is pressed against the wall surface of the organ 100 can be changed, through changing the protrusion length of the elastic region 37 from the distal end 45a of the electrode sheath 45.

During use of the endoscope system 1, when the distal end rigid portion 36 is pressed against the wall surface of the organ 100 and the elastic region 37 elastically deforms, the distal end rigid portion 36 and the electrode 35 move upward within a field of view of the telescope 21. During this operation, the distal end rigid portion 36 and the electrode 35 may move to the outside of the field of view of the telescope 21. In this case, in the present embodiment, the distal end rigid portion 36 and the electrode 35 can be prevented from moving to the outside of the field of view of the telescope 21, by moving the electrode sheath 45 to the distal end side with respect to the proximal end rigid portion 31 to reduce the length by which the elastic region 37 elastically deforms.

Note that the configuration of the electrode supporting portion 32 of the electrode unit 30 of the present embodiment may be any one of the configurations of the first embodiment shown in FIG. 2 to FIG. 30 and the modifications of the first embodiment.

The present invention is not limited to the aforementioned embodiments and can be modified as appropriate without departing from the gist or spirit of the present invention that can be read from the claims and the specification as a whole. An electrode unit and an endoscope system with such a modification is also encompassed in the technical scope of the present invention.

What is claimed is:

1. An electrode unit comprising:
an electrode supporting member comprising:
a pair of distal end rigid members extending along a longitudinal axis, each of the pair of distal end rigid members being covered by an electrically insulating material, and
an elastic region member provided on a proximal end side of each of the pair of distal end rigid members; and
an electrode located between the pair of distal end rigid members, the electrode configured to apply a high-frequency energy to tissue, the electrode comprising a flat portion extending linearly between the pair of distal end rigid members;
wherein a bending rigidity of the elastic region member being such that the elastic region member elastically deforms and is curved relative to the distal end rigid member when the electrode is pressed against a tissue surface;
the electrode is an exposed wire having a surface configured to directly press against the tissue; and
the electrode comprising a pair of base portions directly extending perpendicularly to the longitudinal axis from a respective distal end rigid member of the pair of distal end rigid members toward each other from opposed faces of the pair of distal end rigid members when viewed along the longitudinal axis.

2. The electrode unit according to claim 1, further comprising:
a proximal end rigid member joined to a proximal end of the electrode supporting member; and
an electrical connection portion provided in the proximal end rigid member and electrically connected to the electrode.

3. The electrode unit according to claim 2, further comprising:
a tubular electrode sheath surrounding an outer periphery of the proximal end rigid member; and
an operation member configured to move the electrode sheath to a position for surrounding an outer periphery of the elastic region member.

4. The electrode unit according to claim 1, wherein the flat portion is offset radially from the pair of distal end rigid members, the electrode protrudes from between respective distal ends and proximal ends of the pair of distal end rigid members.

5. The electrode unit according to claim 1, wherein each of the pair of distal end rigid members comprise a concavity that extends in a first direction opposed to a second direction extending between the pair of distal end rigid members, and the electrode protrudes from a respective one of the pair of distal end rigid members in a direction different from the first direction.

6. The electrode unit according to claim 5, wherein the pair of base portions extending from the pair of distal end rigid members, respectively, and each base portion extends in the second direction.

7. The electrode unit according to claim 1, wherein the electrode has a convex shape when viewed along the longitudinal axis and relative to a line connecting distal ends of the pair of distal end rigid members.

8. An endoscope system comprising the electrode unit according to claim 1.

9. The endoscope system according to claim 8, comprising:

a sheath into which the electrode unit is inserted;

a telescope inserted into the sheath;

a slider that holds the telescope on a proximal end side of the sheath in a movable manner in a direction along a longitudinal axis of the sheath; and an electrode unit holding portion that holds the electrode unit on the proximal end side of the sheath in a movable manner in the direction along the longitudinal axis of the sheath, independently of the telescope.

10. The electrode unit according to claim 1, wherein the flat portion protrudes downward from each base portion, the electrode comprises an inclined portion extending from each base portion, and each inclined portion connecting to the flat portion.

11. The electrode unit according to claim 10, wherein each inclined portion has a first end connected to a respective base portion and a second end connected to a respective end of the flat portion.

12. An electrode unit comprising:

an electrode supporting member comprising:

a pair of distal end rigid members extending along a longitudinal axis, each of the pair of distal end rigid members being covered by an electrically insulating material, and an elastic region member having a lower bending rigidity than a bending rigidity of the pair of distal end rigid members, the elastic region member being provided on a proximal end side of each of the pair of distal end rigid members; and an electrode located between the pair of distal end rigid members, the electrode configured to apply a high-frequency energy to a tissue, the electrode comprising:

a flat portion extending linearly between the pair of distal end rigid members; and a pair of base portions directly extending perpendicularly to the longitudinal axis from a respective distal end rigid member of the pair of distal end rigid members toward each other from opposed faces of the pair of distal end rigid members when viewed along the longitudinal axis;

wherein the electrode is an exposed wire having a surface configured to directly press against the tissue.

13. An electrode unit comprising:

a pair of insulators extending along a longitudinal axis; and an elastic portion located on a proximal end side of each of the pair of insulators; and an electrode located between the pair of insulators;

wherein a bending rigidity of the elastic region member being such that the elastic region member elastically deforms and is curved relative to the pair of insulators when the electrode is pressed against a tissue surface;

the electrode is an exposed wire having a surface configured to directly press against the tissue surface; and the electrode comprising a pair of base portions directly extending perpendicularly to the longitudinal axis from a respective insulator of the pair of insulators toward each other from opposed faces of the pair of insulators when viewed along the longitudinal axis.

14. The electrode unit according to claim 13, wherein the electrode includes a flat portion extending linearly between the pair of insulators.

15. The electrode unit according to claim 14, wherein the pair of base portions directly extends from a respective insulator of the pair of insulators, the flat portion is offset radially from the pair of base portions.

* * * * *